United States Patent
Bailey et al.

(10) Patent No.: US 10,667,831 B2
(45) Date of Patent: Jun. 2, 2020

(54) BROADLY FOCUSED ULTRASONIC PROPULSION PROBES, SYSTEMS, AND METHODS

(71) Applicants: University of Washington, Seattle, WA (US); Sonomotion, Inc., Emerald Hills, CA (US)

(72) Inventors: Michael R. Bailey, Seattle, WA (US); Bryan Cunitz, Seattle, WA (US); Barbrina Dunmire, Seattle, WA (US); Adam Maxwell, Seattle, WA (US); Oren Levy, Seattle, WA (US)

(73) Assignees: University of Washington, Seattle, WA (US); Sonomotion, Inc., San Mateo, CA (US)

( * ) Notice: Subject to any disclaimer, the term of this patent is extended or adjusted under 35 U.S.C. 154(b) by 0 days.

(21) Appl. No.: 15/519,821

(22) PCT Filed: Oct. 19, 2015

(86) PCT No.: PCT/US2015/056261
§ 371 (c)(1),
(2) Date: Apr. 17, 2017

(87) PCT Pub. No.: WO2016/061587
PCT Pub. Date: Apr. 21, 2016

(65) Prior Publication Data
US 2017/0245874 A1    Aug. 31, 2017

Related U.S. Application Data

(60) Provisional application No. 62/160,458, filed on May 12, 2015, provisional application No. 62/065,432, filed on Oct. 17, 2014.

(51) Int. Cl.
A61B 8/00    (2006.01)
A61B 17/22   (2006.01)
(Continued)

(52) U.S. Cl.
CPC ........ *A61B 17/22004* (2013.01); *A61B 8/085* (2013.01); *A61N 7/02* (2013.01);
(Continued)

(58) Field of Classification Search
None
See application file for complete search history.

(56) References Cited

U.S. PATENT DOCUMENTS 5,558,092 A * 9/1996 Unger .................. A61B 8/0833
                                              600/439
5,743,862 A * 4/1998 Izumi ................. A61B 17/2258
                                              310/334
(Continued)

FOREIGN PATENT DOCUMENTS

JP    05-058110 U    8/1993
JP    2006204929 A   8/2006
(Continued)

OTHER PUBLICATIONS

Shah, A., Harper, J. D., Cunitz, B. W., Wang, Y., Paun, M. Simon, J. C., Lu, W. , Kaczkowski, P. J., and Bailey, M. R., "Focused Ultrasound to Expel Calculi From the Kidney", The Journal of Urology, vol. 187, pp. 739-743, Feb. 2012.*
(Continued)

*Primary Examiner* — Joanne M Hoffman
(74) *Attorney, Agent, or Firm* — Christensen O'Connor Johnson Kindness PLLC

(57) ABSTRACT

Disclosed herein are ultrasonic probes and systems incorporating the probes. The probes are configured to produce an ultrasonic therapy exposure that, when applied to a kidney stone, will exert an acoustic radiation force sufficient to produce ultrasonic propulsion. Unlike previous probes configured to produce ultrasonic propulsion, however, the disclosed probes are engineered to produce a relatively large
(Continued)

(both wide and long) therapy region effective to produce ultrasonic propulsion. This large therapy region allows the probe to move a plurality of kidney stones (or fragments from lithotripsy) in parallel, thereby providing the user the ability to clear several stones from an area simultaneously. This "broadly focused" probe is, in certain embodiments, combined in a single handheld unit with a typical ultrasound imaging probe to produce real-time imaging. Methods of using the probes and systems to move kidney stones are also provided.

20 Claims, 16 Drawing Sheets

(51) Int. Cl.
*A61N 7/02* (2006.01)
*A61B 8/08* (2006.01)
*A61B 17/225* (2006.01)
*A61B 18/00* (2006.01)

(52) U.S. Cl.
CPC . *A61B 17/2258* (2013.01); *A61B 2017/22005* (2013.01); *A61B 2018/00023* (2013.01); *A61B 2018/00511* (2013.01)

(56) References Cited

U.S. PATENT DOCUMENTS

| | | | | |
|---|---|---|---|---|
| 9,241,761 | B2* | 1/2016 | Rankin | A61B 18/1492 |
| 2001/0051131 | A1* | 12/2001 | Unger | A61K 49/223 424/9.5 |
| 2003/0078227 | A1* | 4/2003 | Greenleaf | A61K 41/0047 514/44 R |
| 2004/0059220 | A1* | 3/2004 | Mourad | A61B 5/0048 600/442 |
| 2005/0228284 | A1* | 10/2005 | Baumgartner | A61B 5/6844 600/459 |
| 2007/0041961 | A1* | 2/2007 | Hwang | A61K 38/363 424/94.64 |
| 2007/0055179 | A1* | 3/2007 | Deem | A61K 41/0028 601/2 |
| 2007/0197914 | A1* | 8/2007 | Kosaku | A61B 8/0841 600/459 |
| 2007/0252999 | A1* | 11/2007 | Hogan | A61B 5/0066 356/450 |
| 2008/0064959 | A1* | 3/2008 | Kanda | G01S 7/52023 600/459 |
| 2008/0091125 | A1* | 4/2008 | Owen | A61B 17/2256 601/4 |
| 2008/0195003 | A1* | 8/2008 | Sliwa | A61N 7/02 601/3 |
| 2008/0319356 | A1* | 12/2008 | Cain | A61B 17/22004 601/2 |
| 2008/0319375 | A1* | 12/2008 | Hardy | A61K 9/0009 604/22 |
| 2009/0177085 | A1* | 7/2009 | Maxwell | A61B 17/22004 600/439 |
| 2009/0230823 | A1* | 9/2009 | Kushculey | A61N 7/02 310/366 |
| 2010/0143241 | A1* | 6/2010 | Johnson | A61K 41/0028 424/1.11 |
| 2010/0274136 | A1* | 10/2010 | Cerofolini | B06B 1/0622 600/459 |
| 2011/0077520 | A1* | 3/2011 | Osawa | A61B 5/01 600/443 |
| 2011/0208095 | A1* | 8/2011 | Jolesz | A61N 7/00 601/2 |
| 2011/0251528 | A1* | 10/2011 | Canney | A61N 7/02 601/3 |
| 2011/0263967 | A1* | 10/2011 | Bailey | A61B 17/2256 600/411 |
| 2013/0047728 | A1 | 2/2013 | Cochran et al. | |
| 2013/0122564 | A1 | 5/2013 | Kimmel et al. | |
| 2013/0122654 | A1 | 5/2013 | Kimmel et al. | |
| 2013/0172742 | A1 | 7/2013 | Rankin et al. | |
| 2013/0237820 | A1 | 9/2013 | Vappou et al. | |
| 2013/0261442 | A1* | 10/2013 | Yang | A61M 37/0092 600/431 |
| 2015/0196638 | A1* | 7/2015 | Czarnota | A61N 5/10 600/1 |
| 2015/0327835 | A1* | 11/2015 | Kim | A61B 8/48 600/438 |
| 2016/0262727 | A1* | 9/2016 | Dayton | A61B 8/4477 |

FOREIGN PATENT DOCUMENTS

| | | |
|---|---|---|
| JP | 2013527782 | 7/2013 |
| WO | 2014008594 A1 | 1/2014 |

OTHER PUBLICATIONS

Harper, J. D., Sorensen, M. D., Cunitz, B. W., Wang, Y., Simon, J. C., Starr, F., Paun, M., Dumire, B., Liggitt, H. D., Evan, A. P., McAteer, J. A., His, R. S., and Bailey, M. R., "Focused Ultrasound to Expel Calculi From the Kidney: Safety and Efficacy of a Clinical Prototype Device", The Journal of Urology, vol. 190, pp. 1090-1095, Sep. 2013.*

Michael R. Bailey, Yak-Nam Wang, Julianna Simon, Bryan Cunitz, Jonathan Harper, Ryan Hsi, Frank Starr, Marla Paun, Oleg Sapozhnikov, Barbrina Dunmire, Lawrence Crum, and Mathew Sorensen, "Acoustic radiation force to reposition kidney stones", Proc Meet Acoust. 2013; 19.*

APL, University of Washington, http://www.apl.washington.edu/project/project.php?id=pushing_stones and https://youtu.be/n6sCy2ZTjbE, May 2, 2013.*

Basic Principle of medical ultrasonic probes (transducers); Portal Site of Ultrasonic Sensors, Ultrasonic Tecnology.*

International Search Report and Written Opinion dated Jan. 5, 2016, issued in corresponding International Application No. PCT/US2015/056261, filed Oct. 19, 2015, 7 pages.

International Preliminary Report on Patentability dated Apr. 18, 2017, issued in corresponding International Application No. PCT/US2015/056261, filed Oct. 19, 2015, 7 pages.

Notice of Reasons for Refusal, received on May 29, 2018 in related Japanese Patent Application No. 2017-539527, filed Apr. 14, 2017 with English Translation, 7 pages.

Extended European Search Report, dated Jun. 7, 2018 in related European Patent Application No. 15851498.4, filed Apr. 4, 2017, 7 pages.

Bibliographic Data of the European Patent Application dated Dec. 10, 2018, issued in corresponding Application No. 15851498.4, filed Oct. 19, 2015, 2 pages.

Communication About Intention to Grant a European Patent dated Dec. 10, 2018, issued in corresponding Application No. 15851498.4, filed Oct. 19, 2015, 5 pages.

Intent to Grant (Signatures) dated Dec. 10, 2018, issued in corresponding Application No. 15851498.4, filed Oct. 19, 2015, 1 page.

Text Intended to Grant dated Dec. 10, 2018, issued in corresponding Application No. 15851498.4, filed Oct. 19, 2015, 83 pages.

Amended Claims for Responding to Office Action of May 22, 2018, filed Jul. 27, 2018 in corresponding Japanese Application No. 2017-539527, filed Oct. 19, 2015, 13 pages.

Certificate of Patent Registration dated Oct. 23, 2018, issued in corresponding Japanese Application No. 2017-539527, filed Oct. 19, 2015, 4 pages.

Grant of Invention Patent Notice dated May 24, 2019, issued in corresponding Chinese Application No. 201580061007.7, filed Oct. 19, 2015, 3 pages.

State Intellectual Property Office Search Report dated May 24, 2019, issued in corresponding Chinese Application No. 201580061007.7, filed Oct. 19, 2015, 4 pages.

* cited by examiner

BROADLY FOCUSED ULTRASONIC PROPULSION PROBES, SYSTEMS, AND METHODS

CROSS-REFERENCES TO RELATED APPLICATIONS

This application claims the benefit of U.S. Patent Application No. 62/065,432, filed Oct. 17, 2014, and U.S. Patent Application No. 62/160,458, filed May 12, 2015, the disclosure of each of which are hereby incorporated by reference in its entirety.

STATEMENT OF GOVERNMENT LICENSE RIGHTS

This invention was made with Government support under grants R01 DK092197 and P01 DK043881, awarded by the National Institutes of Health; and under grant SMST03402, awarded by the National Space Biomedical Research Institute. The Government has certain rights in the invention.

BACKGROUND

The disclosed embodiments address the need to safely facilitate the expulsion of kidney stones from an afflicted patient. The National Institute of Diabetes and Digestive and Kidney Diseases (NIDDK) Urinary Stone Disease Research Opportunities and Challenges (USDROC) Workshop website characterizes the problem as follows: "Urinary Stone Disease (USD) is an important health care problem affecting both adults and children, causing pain and suffering for the patient and a financial burden to the Nation. One in 11 Americans now has USD, and the prevalence is increasing. According to the NIDDK-funded study, Urological Diseases in America, the direct medical cost of USD in the United States is $10 billion annually, making it the most expensive urologic condition." Residual fragments are widely considered to be the overwhelming clinical and research priority in USD, because current treatment options, such as shock wave lithotripsy (SWL) or ureteroscopic lithotripsy (URS), leave behind small residual stone fragments. Studies have shown that while most residual stone fragments will pass, others may grow and in approximately 20% to 40% of patients, lead to symptomatic events such as pain, emergency room visits, or additional procedures. Yet until now no tool or methods exist by which a large number of residual stone fragments can be manipulated (in parallel) within a patient. The primary viable option is presently the serial use of focused ultrasound to manipulate one stone at a time. However, for a large number of small stones this serial method is unfeasible. Accordingly, new tools and method for manipulating a plurality of kidney stones within a patient are desirable.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, an ultrasonic therapy system configured to apply a non-lithotriptic acoustic radiation force to a kidney stone is provided. In one embodiment, the ultrasonic therapy system, comprises:

(a) a therapy probe configured to generate ultrasonic exposure directed towards a therapy region; and (b) an imaging probe configured to ultrasonically image the therapy region;

wherein the therapy probe is configured to produce a therapy exposure comprising one or more therapy pulses over a therapy exposure time, wherein the therapy exposure has the following characteristics:

(i) a frequency of 100 kHz to 1 MHz;

(ii) therapy exposure time of at least 10 ms;

(iii) a peak negative pressure in the therapy region of 0.5 MPa to 5 MPa;

(iv) the therapy region of one pulse defining a volume subjected to a full-width half-maximum pressure or greater and the therapy region having a length of 2 cm or greater in an axial direction and 2 mm or more in width; and (v) the therapy region is sufficient to exert an acoustic radiation force on a kidney stone having a diameter of from 0.5 mm to 20 mm disposed within the therapy region, wherein the acoustic radiation force applied to the kidney stone is from 50 $\mu$N to 0.5 N, and wherein the acoustic radiation force is not sufficient to fragment the kidney stone.

In another aspect, a method of moving one or more target objects using ultrasonic propulsion is provided. In one embodiment, the method includes applying a non-lithotriptic acoustic radiation force to a target object using an ultrasonic therapy system as shown and described herein.

In another aspect, a method of moving one or more kidney stones in a therapy region using ultrasonic propulsion is provided. In one embodiment, the method includes using a broadly focused ultrasound therapy probe to apply a force on one or more kidney stones having a diameter of from 0.5 mm to 20 mm disposed within the therapy region, wherein the acoustic radiation force applied to each of the one or more kidney stones is from 50 $\mu$N to 0.5 N, and wherein the acoustic radiation force is not sufficient to fragment the kidney stones.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
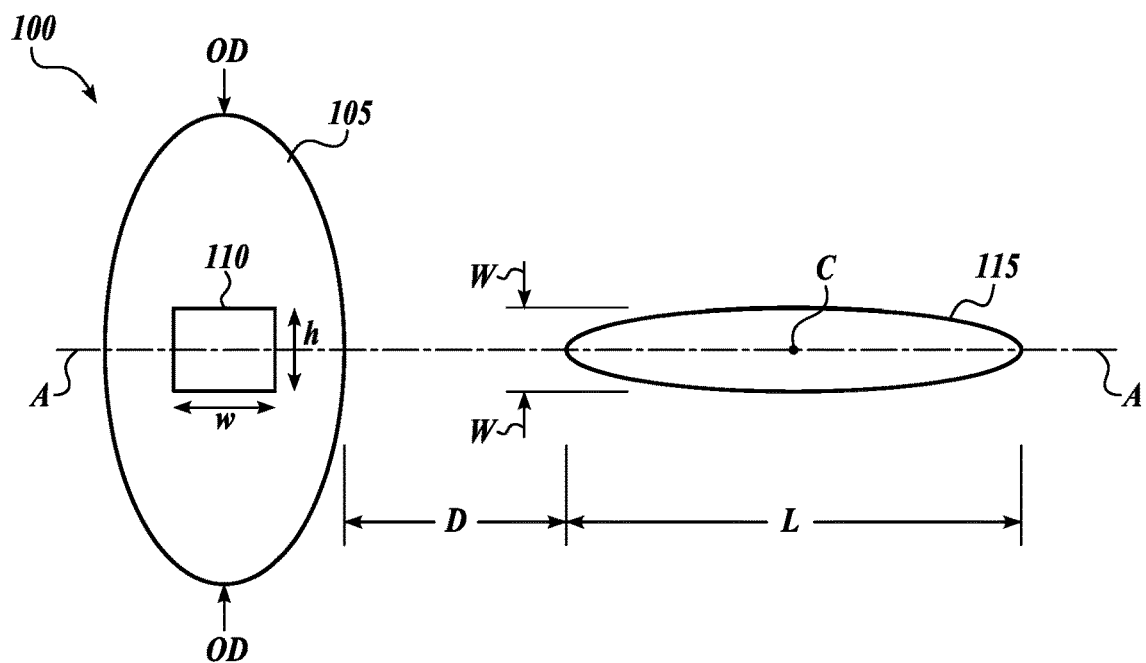
FIG. 1A illustrates the relationship between a therapy probe, an imaging probe, and a therapy region of an ultrasonic therapy system in accordance with embodiments disclosed herein.

Disclosed herein are ultrasonic therapy probes and systems incorporating the probes. The probes are configured to produce an ultrasonic therapy exposure that, when applied to a kidney stone, will exert an acoustic radiation force sufficient to produce ultrasonic propulsion. Unlike previous probes configured to produce ultrasonic propulsion, however, the disclosed probes are engineered to produce a relatively large (both wide and long) therapy region effective to produce ultrasonic propulsion. This large therapy region allows the probe to move a plurality of kidney stones (or fragments from lithotripsy) in parallel, thereby providing the user the ability to clear several stones from an area simultaneously. This "broadly focused" probe is, in certain embodiments, combined in a single handheld unit with a typical ultrasound imaging probe. By coordinating the ultrasound signals produced by both the therapy probe and the imaging probe a user of the combined probe can image stones in real time as the broadly focused ultrasound moves stones within a patient. Methods of using the probes and systems to move kidney stones are also provided.

Advantages of the disclosed broadly focused beam include easier alignment. The wide beam yields a greater probability of targeting a stone. The relatively long therapy region accounts for the difficulty in changing focal depth during use, therefore simplifying targeting. Furthermore, the disclosed system allows for simpler cheaper systems, particularly in embodiments that utilize a single therapy transducer ("fixed focus"). Finally, the disclosed embodiments, during treatment, yield no "hot spots" of high amplitude (>−6 dB compared to focal pressure), making the devices and methods safer and more predictable when applied to patients.

In one aspect, an ultrasonic therapy system configured to apply a non-lithotriptic acoustic radiation force to a kidney stone is provided. In one embodiment, the ultrasonic therapy system, comprises:

(a) a therapy probe configured to generate ultrasonic exposure directed towards a therapy region; and (b) an imaging probe configured to ultrasonically image the therapy region;

wherein the therapy probe is configured to produce a therapy exposure comprising one or more therapy pulses over a therapy exposure time, wherein the therapy exposure has the following characteristics:

(i) a frequency of 100 kHz to 1 MHz;
(ii) therapy exposure time of at least 10 ms;
(iii) a peak negative pressure in the therapy region of 0.5 MPa to 5 MPa;
(iv) the therapy region of one pulse defining a volume subjected to a full-width half-maximum pressure or greater and the therapy region having a length of 2 cm or greater in an axial direction and 2 mm or more in width; and
(v) the therapy region is sufficient to exert an acoustic radiation force on a kidney stone having a diameter of from 0.5 mm to 20 mm disposed within the therapy region, wherein the acoustic radiation force applied to the kidney stone is from 50 μN to 0.5 N, and wherein the acoustic radiation force is not sufficient to fragment the kidney stone.

The ultrasonic system may be better understood by referencing the diagrammatic illustration of FIG. 1A, which illustrates a combined probe 100 including both a therapy probe 105 and an imaging probe 110. Disposed along axis A of both probes 105 and 110 is the therapy region 115.

The therapy region 115 is defined herein as the volume of space (e.g., within a patient) subjected to a full-width half-maximum (FWHM) pressure or greater. In this regard, the therapy probe 105 will produce a maximum pressure at a certain point in the therapy region 115 and the boundaries of the therapy region 115 are defined by the region wherein the pressure is FWHM in view of the maximum pressure. The therapy region 115 has a center point C, a length L, and a width W, and begins a distance D from the therapy probe 105. As used herein, the therapy region "width" is defined as the distance between the locations in the field orthogonal to the acoustic axis A where the pressure reaches −6 dB relative to the peak focal pressure.

The therapy probe 115 is annular (at least roughly circular) as depicted in FIG. 1A, having an outside dimension OD. The therapy probe 115 is circular in one embodiment. The imaging probe 110 is typically rectangular, having a height h and width w. The sizes of the combined probe 100 and, relatedly, the therapy probe 105 and imaging probe 110, are of great importance. The combined probe 100 must be compact (e.g., OD of 5 cm or less) in order to be easily handheld by an operator and to be maneuverable to position at any point along a patient's skin. These dimensional constraints lead to the coaxial combination of the probes 105 and 110 to form the compact combined probe 100. An exemplary combined probe 100 is pictured in FIG. 1B.

Figure 1B:
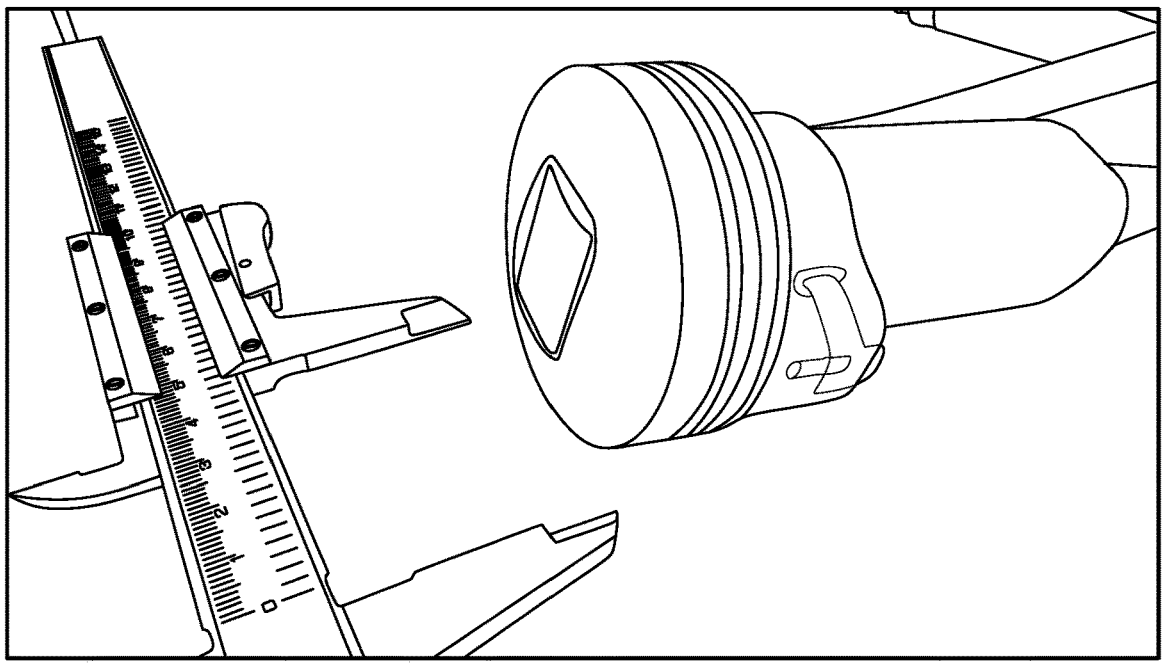
FIG. 1B is a photograph of a prototype combination therapy probe (annular) and imaging probe (center) in accordance with embodiments disclosed herein.
Figure 1C:
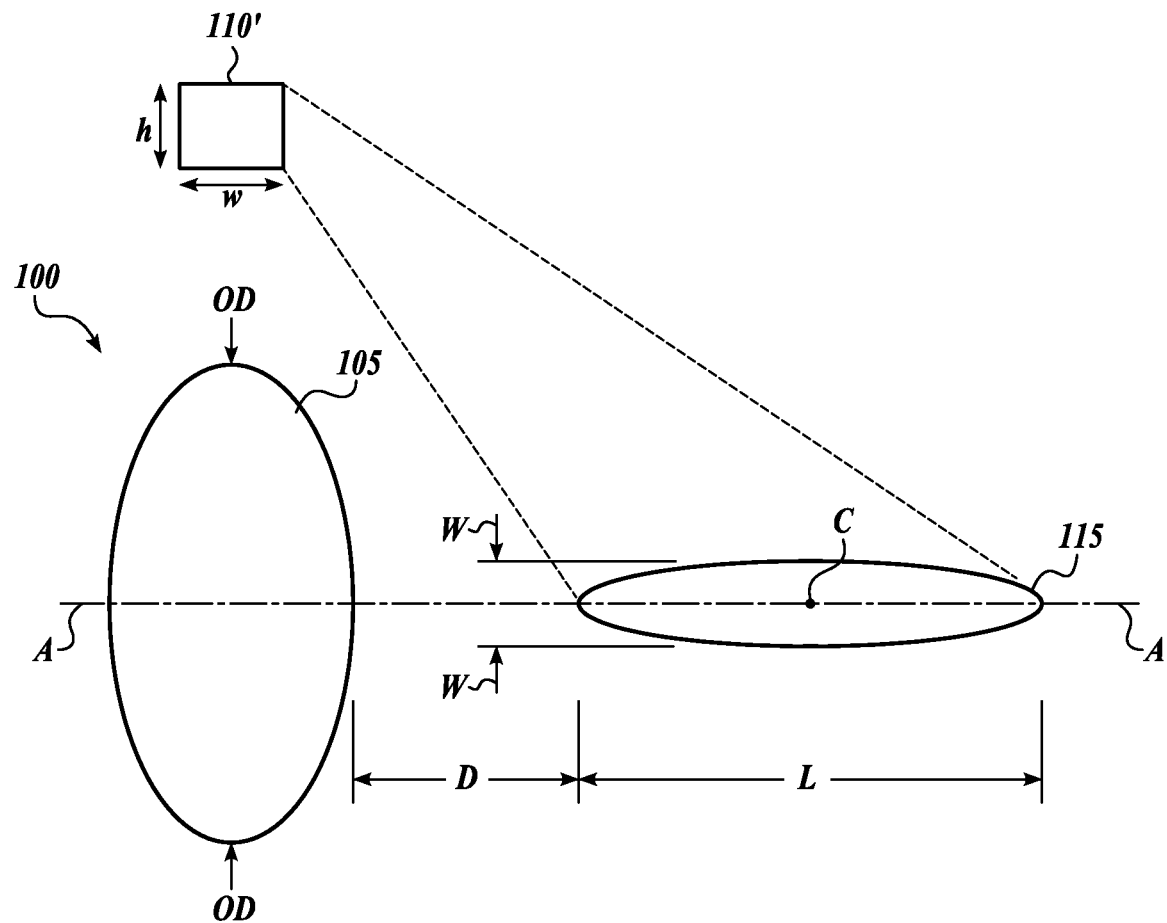
FIG. 1C illustrates another embodiment of a therapy system, wherein the therapy probe and imaging probe are separately arranged but both focused on the therapy region.

In an embodiment of the system distinct from that of FIGS. 1A and 1B, FIG. 1C illustrates a system without an integrated imaging probe 110. Instead, a separately disposed imaging probe 110' is utilized. The imaging probe 110' is still coordinated with the therapy probe 105 during use and is still focused on the therapy region 115. However, the imaging probe 110' is not coaxially disposed on axis A. This arrangement does not provide the benefits of ease of use when coaxially focusing on the therapy region 115, although this embodiment may be more easily fabricated from off-the-shelf components because a custom coaxial probe (e.g., combined probe 100) need not be fabricated.

Figure 2:
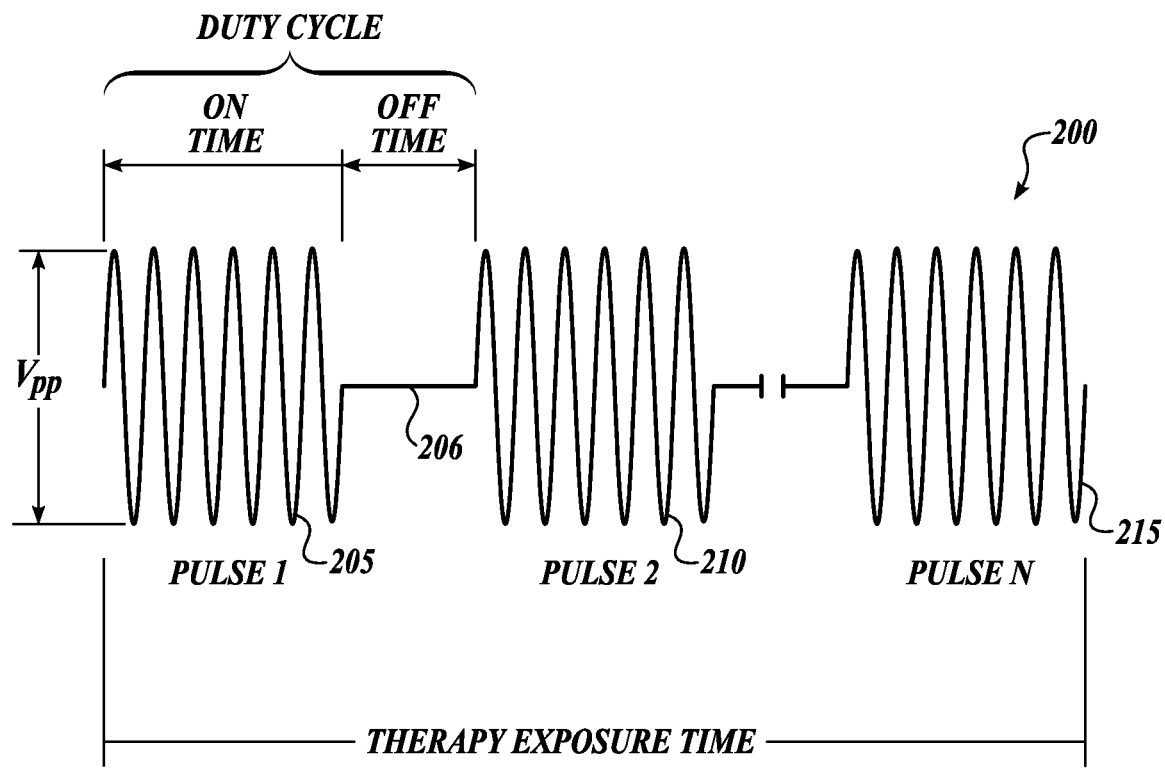
FIG. 2 illustrates an exemplary ultrasonic therapy exposure in accordance with embodiments disclosed herein.
Figure 3:
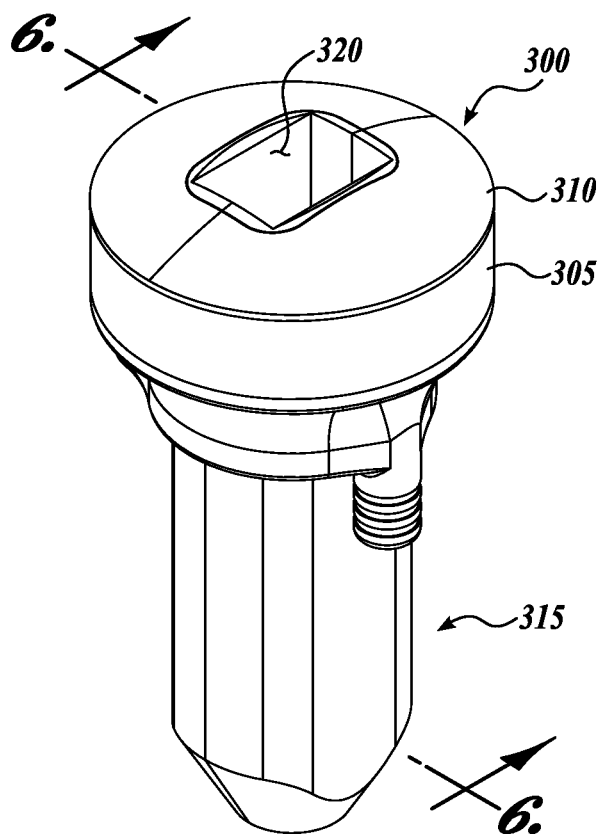
FIGS. 3-6 illustrate an exemplary therapy probe in accordance with embodiments disclosed herein.
Figure 4:
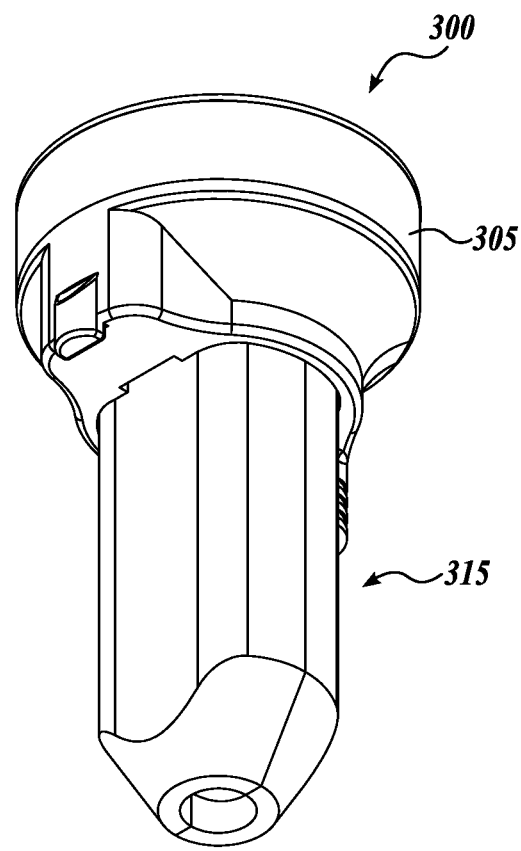
Figure 5:
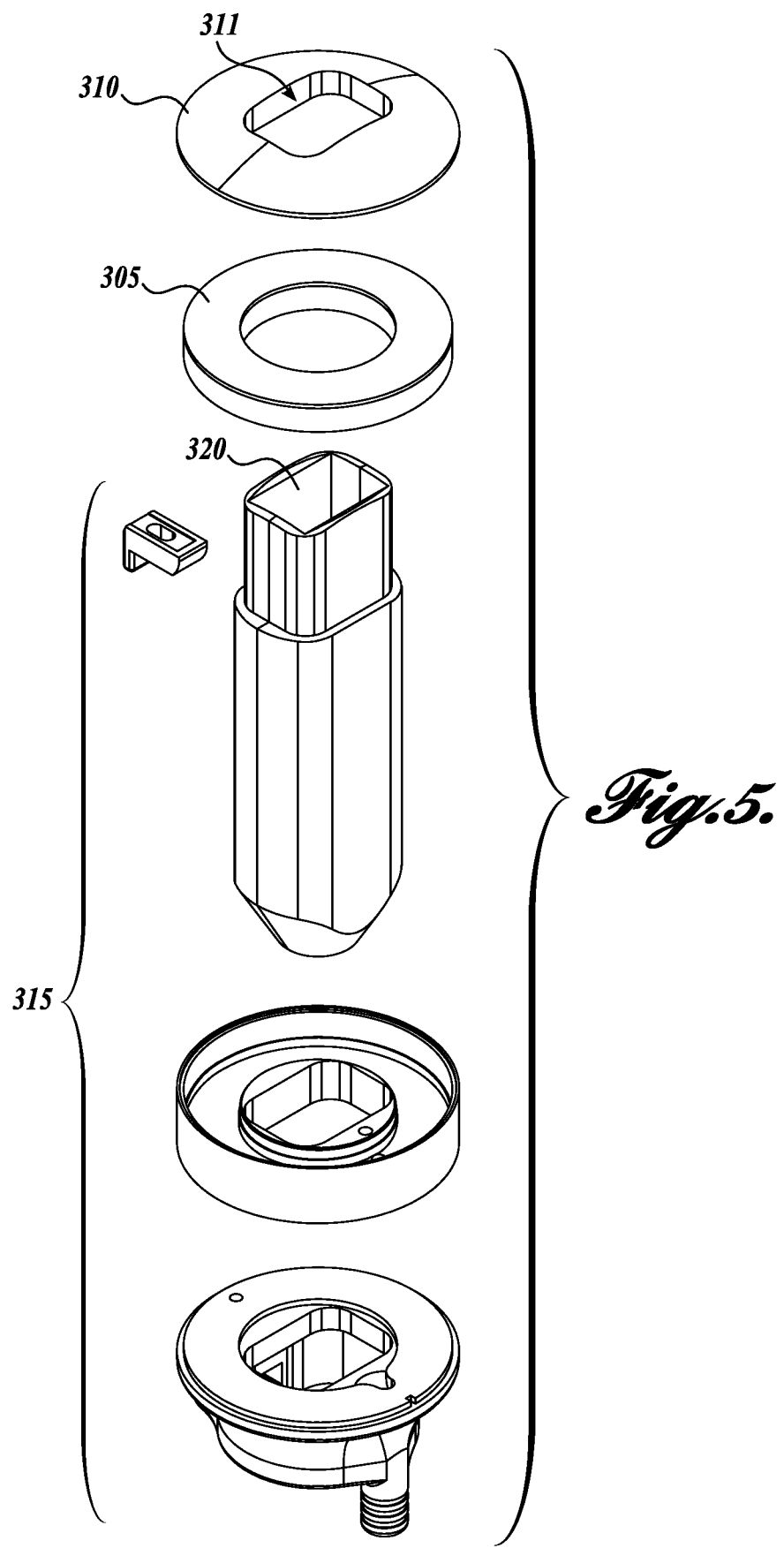

During operation, the therapy probe 105 emits a therapy exposure comprising one or more ultrasonic therapy pules over a therapy exposure time (refer to FIG. 2 for a visual illustration of the therapy exposure signal). If imaging is utilized, the therapy probe 105 and imaging probe 110 are coordinated such that their signals do not overlap yet images are acquired frequently enough (e.g., at least one frame per second, fps). By acquiring images of the therapy region 115 during a therapy exposure, the operator can see the movement of stones in real time and adjust aim and/or focus as needed to accomplish the treatment (e.g., move the stones towards expulsion from the kidney or other region).

The term "therapy exposure" relates herein to a series of pulses over an exposure time. The exposure time is defined in certain embodiments by a user activating the therapy probe by an on switch or other mechanism. An exemplary mechanism is on on/off switch, such as a foot-activated switch. Several therapy exposures may be utilized by a user during treatment of a patient for a cumulative therapy exposure session. Therapy exposures end when the system is continuously off for a prolonged period (e.g., 1 second or greater). An "off" period between pulses (i.e., when the duty cycle is less than 100%) does not mark the end of a therapy exposure.

The ultrasonic therapy system is non-lithotriptic and therefore the ultrasound applied by the system is not sufficient to break a kidney stone. The purpose of the system is to provide a relatively large therapy region in which the therapy probe produces sufficient acoustic radiation force to move any kidney stones within the therapy region. While the description herein discusses the unusual utility of the systems in moving a plurality of stones or fragments, it will be appreciated that the movement of a single stone, even a single large stone is also contemplated in certain embodiments. As an example, a single large stone may be moved that is blocking the ureter.

The therapy exposure is an ultrasonic signal as depicted in FIG. 2. It can be defined by a number of parameters, including frequency, therapy exposure time, the peak negative pressure in the therapy region, power, intensity, and driving voltage.

The therapy region is sufficient to exert an acoustic radiation force on a kidney stone having a diameter of from 0.5 mm to 20 mm disposed within the therapy region, wherein the acoustic radiation force applied to the kidney stone is from 50 µN to 0.5 N, and wherein the acoustic radiation force is not sufficient to fragment the kidney stone. This characteristic of the system and therapy region indicates the nature of the force exerted by the therapy probe: non-lithotriptic and "pushing" using an acoustic radiation force. The acoustic radiation force can be measured experimentally in vitro (e.g., on the bench) using an acoustic radiation force balance or load cell, a radiation force radiometer, or any other technique known to those of skill in the art.

Figure 6:
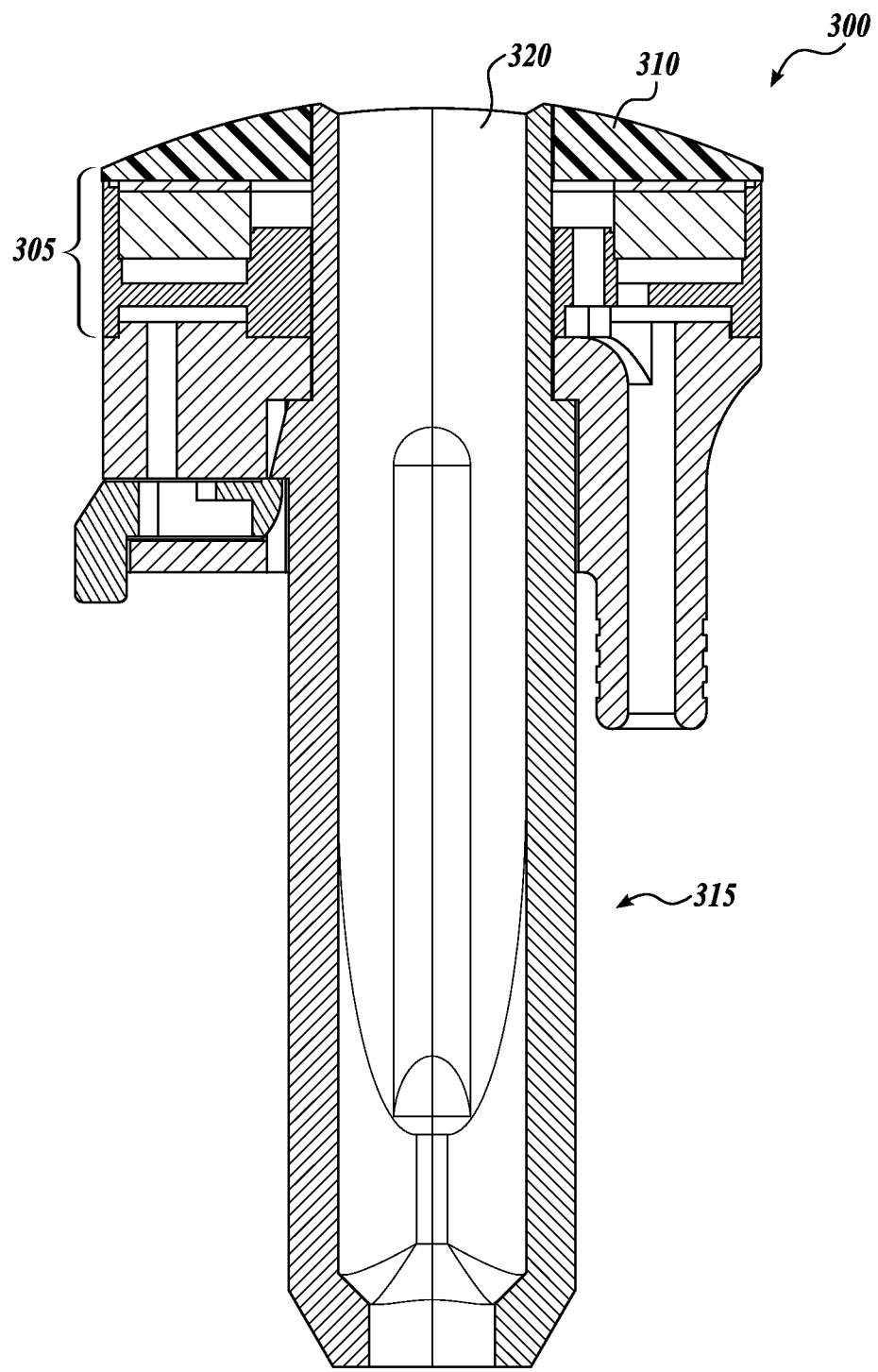

The combined probe 100 has a handheld form factor for ease of clinical use. An exemplary combined probe 100 is pictured in FIG. 1B and FIGS. 3-6 are line drawings depicting the housing and therapy probe. Referring now to FIGS. 3-6, the housing 300 includes a therapy probe transducer 305 a lens 310, an elongate handle 315, and a housing 320 configured to hold an imaging probe, which fits through the lens 310 and therapy transducer 305 via an aperture 311 in each. FIG. 6 is a cross-sectional view of the housing 300.

In the exemplary embodiments the therapy probe transducer 305 is a custom PZT transducer and the imaging probe is a commercial imaging probe. However, it will be appreciated that in other embodiments both probes are custom made or both are commercially available.

Figures 7A, 7B:
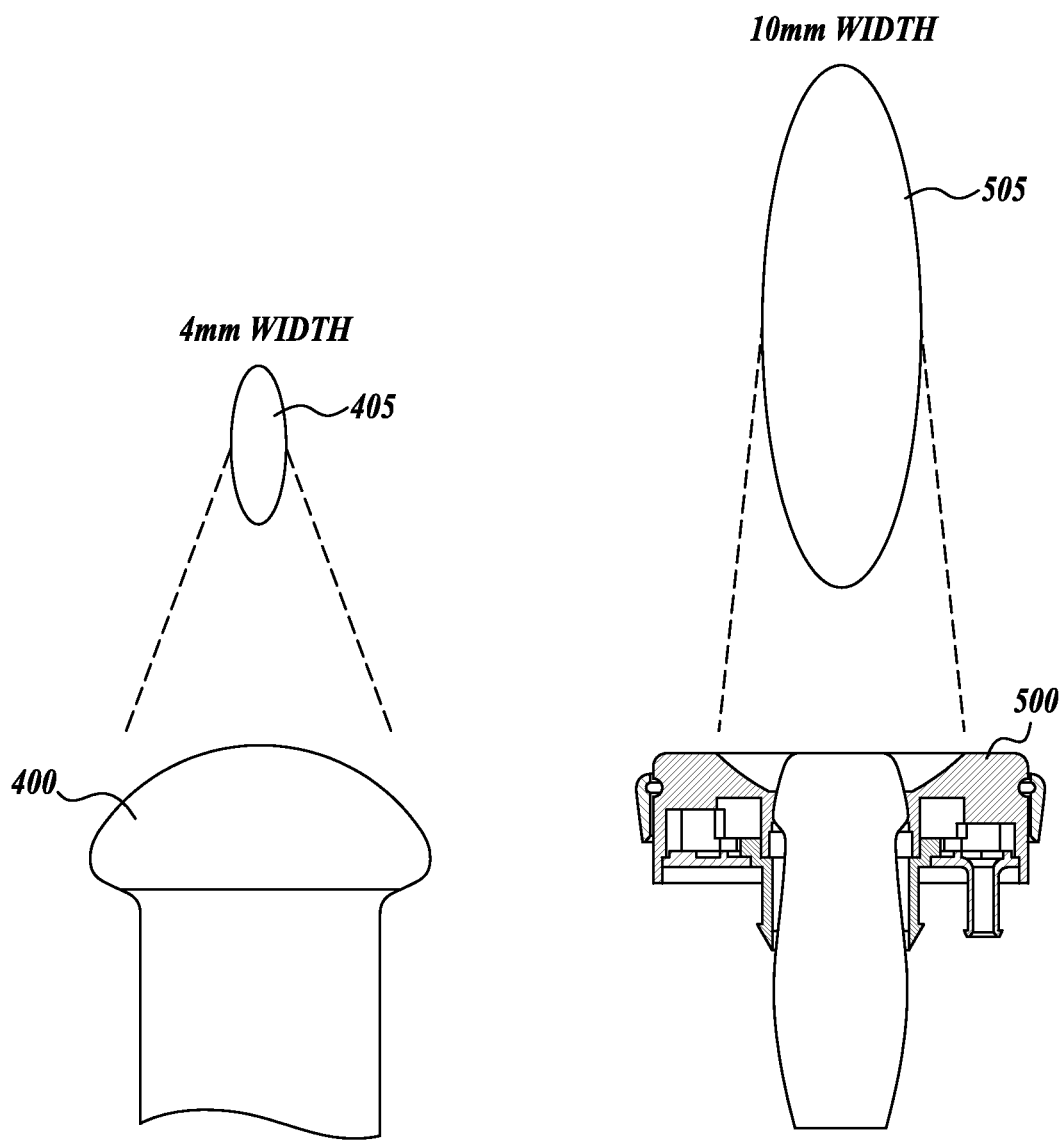
FIGS. 7A and 7B illustrate the therapy region sizes generated by a prior art probe (FIG. 7A) and a therapy probe in accordance with embodiments disclosed herein (FIG. 7B)

FIGS. 7A and 7B compare the relative therapy region sizes of a commercial therapy probe (FIG. 7A) compared to the broadly focused therapy probe disclosed herein (FIG. 7B). The size of the therapy region can be an order of magnitude larger, which allows for a broader push on a plurality of stones or fragments.

It should be noted that while the disclosed embodiments are described in the context of moving kidney stones (or fragments thereof) using broadly focused ultrasound, the concepts disclosed herein can also be used to move other embedded objects, including, but not limited to, stones, fragments, blood clots, bullets, mucous, cystic fibrosis mucous, flowing blood, impacted stool in constipation, rectal, urethral and bladder foreign bodies, ureteral stones, bladder stones, airway foreign bodies, nasal congestion, sinus obstruction, impacted cerumen (ear wax), tissue flaps (like a torn retina), or floating objects in the eye and dust located in any of the gall bladder, the salivary tract, biliary tract or any other anatomical location, of a human or other mammal. An additional use for the disclosed embodiments is to become a part of the maintenance program of implanted foreign bodies to prevent encrustation or occlusion over time. For example, ureteral stents become encrusted from urine solutes precipitating over time on the surface of the stent. The stent could receive intermittent pushing every 3 weeks to "disrupt" or slow the encrustation process. A similar embodiment could be envisioned for cardiac stents."

As used herein, the term "about" indicates that the subject value can be modified by plus or minus 5% and still fall within the disclosed embodiment. Additionally, stated values are in situ. Relatedly, the term "derated" used herein means measured in the water tank and extrapolated to values in situ. Equations for producing derated ultrasonic values are known to those of skill in the art. For example, the equation X (derated pressure in MHz)=0.03 db/cm/MHz*depth of tissue penetration (cm)*MHz center frequency of pulse*initial amplitude of the focal pressure measured in water (MPa)*Np/8.7 db (Np=neper).

Specific aspects of the ultrasonic therapy system and methods will now be described in further detail.

Therapy Probe Characteristics

The therapy probe is an ultrasonic transducer. Ultrasonic transducers are generally known in the art and are formed from piezoelectric materials, such as lead zirconate titanate (PZT).

In one embodiment, the pulses have a duration of 1 ms to 350 ms. In a further embodiment, the pulses have a duration of 10 ms to 200 ms. In yet a further embodiment, the pulses have a duration of 50 ms to 200 ms. An exemplary embodiment utilizes 25 ms pulse durations.

350 ms is an upper pulse duration limit due to the desire to coordinate the therapy probe with the imaging probe. The imaging probe should not be receiving signals to make an image when the therapy probe is transmitting, and so a therapy pulse must be turned "off" in order to make time for an imaging pulse. This relationship may be better understood with reference to FIG. 2, which illustrates a therapy exposure 200 comprising a number of pulses 205, 210, 215. Each pulse 205 et al. has an on time which is followed by an off time 206 in which the imaging probe can operate to produce at least two frames per second. This frame rate, while low, still allows an operator to track kidney stones exposed to the therapy exposure sufficiently.

In an alternative embodiment, imaging is not used during therapy exposure. However, imaging the therapy region provides significant benefits to use.

The total time over which the therapy probe operates is referred to as the "therapy exposure time." The duty cycle is defined as the percentage of on time compared to total on time and off time before a new pulse begins.

Due to the low frequency and power of the therapy probe, a 100% duty cycle is possible, although imaging in such a situation must be accomplished in a manner that does not interfere with the therapy probe. Accordingly, in one embodiment the therapy exposure is a single continuous pulse.

Average power is another characteristic useful for defining the therapy probe and the therapy exposure. Average power is defined as the total power emitted over the active area of the probe averaged over the duration of the therapy exposure. In one embodiment, the therapy probe is configured to produce an average power of 5 W to 200 W for 1 second to 10 min. In one embodiment, the therapy probe is configured to produce an average power of 10 W to 200 W for 1 second to 10 min. In one embodiment, the therapy probe is configured to produce an average power of 15 W to 60 W for 1 second to 10 min.

In one embodiment, the therapy region is defined by a single therapy pulse. The definitions described herein of beam width are for exposure to one focus. This is in contrast to a system that uses a sequence of pulses focused on different points to broaden the total exposed width. The width used herein is the width of a beam at a snapshot in time. It is not the width constructed by a succession of pulses.

In one embodiment, the therapy region has a length of 2 cm to 15 cm. In one embodiment, the therapy region has a length of 4 cm to 10 cm. In one embodiment, the therapy region has a length of 3 cm or greater. In one embodiment, the therapy region has a length of 5 cm or greater. In one embodiment, the therapy region has a length of 15 cm or less.

In one embodiment, the therapy region has a width of 2 mm to 20 mm. In one embodiment, the therapy region has a width of 1 mm to 10 mm. In one embodiment, the therapy region has a width of 5 mm to 8 mm. In one embodiment, the therapy region has a width of greater than 3 mm. In one embodiment, the therapy region has a width of greater than 5 mm. In one embodiment, the therapy region has a width of less than 10 mm. In one embodiment, the therapy region has a width of less than 20 mm.

In one embodiment, the therapy region has a width of at least 1 mm and a length of at least 2 cm; In one embodiment, the therapy region has a width of at least 2 mm and a length of at least 1 cm. In one embodiment, the therapy region has a width of at least 1 mm and a length of at least 1 cm.

In one embodiment, the frequency is 200 kHz to 500 kHz. In one embodiment, the frequency is 300 kHz to 450 kHz.

In one embodiment, the peak negative pressure in the therapy region is 1.0 MPa to 4.0 MPa. In one embodiment, the peak negative pressure in the therapy region is 1.5 MPa to 3.5 MPa.

In one embodiment, the therapy region begins at least 1 cm from the therapy probe. In one embodiment, the therapy region begins at least 3 cm from the therapy probe. In one embodiment, the therapy region begins at least 5 cm from the therapy probe.

In one embodiment, the therapy exposure is at least 1 second long. In one embodiment, the therapy exposure is at least 10 seconds long. In one embodiment, the therapy exposure is at least 30 seconds long. In one embodiment, the therapy exposure is at least 60 seconds long. In one embodiment, the therapy exposure is at least 5 minutes long. In one embodiment, the therapy exposure is at least 10 minutes long.

In one embodiment, the therapy exposure comprises a therapy burst that comprises a plurality of pulses separated by off periods. This configuration is illustrated in FIG. 2.

In one embodiment, the therapy burst has a duty cycle of greater than 30%. In one embodiment, the therapy burst has a duty cycle of greater than 50%. In one embodiment, the therapy burst has a duty cycle of greater than 75%.

Figure 13:
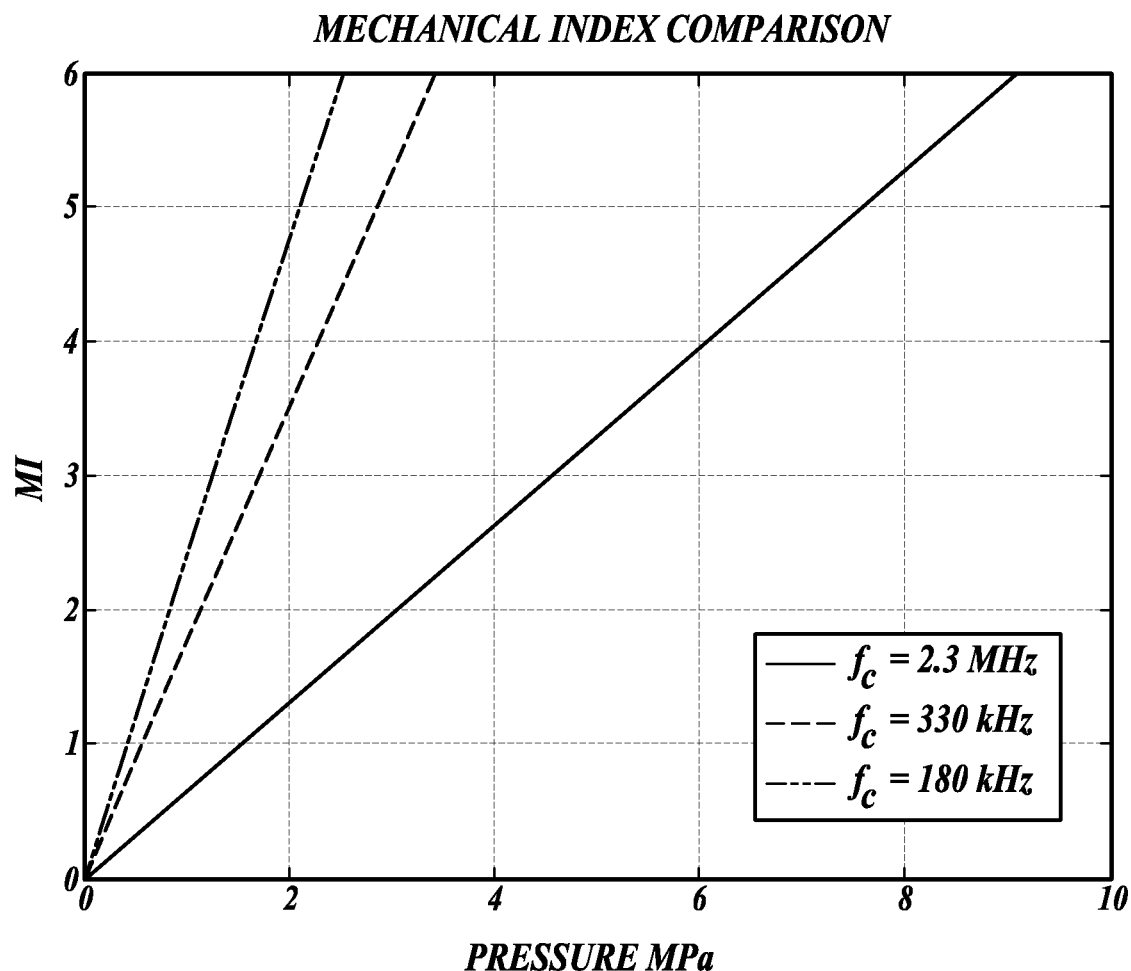
FIG. 13 graphically illustrates the correlation between mechanical index (MI), pressure, and frequency of an ultrasound system.

The disclosed system operates within defined ranges of mechanical index. Mechanical index is defined herein as peak negative pressure (MPa)/square root of frequency (in MHz). FIG. 13 graphically illustrates the correlation between mechanical index (MI), pressure, and frequency of an ultrasound system. In one embodiment, the mechanical index is 10 or below, which is the upper limit before stone fragmentation is likely occur. In one embodiment, the mechanical index is 4 or below, which is an FDA limit related to imaging. In one embodiment, the mechanical index is 1.9 or below, which is a lower FDA limit.

Probe Shapes

In one embodiment, the therapy probe has a largest aperture dimension (e.g., FIG. 1A OD) that is 5 cm or less. In one embodiment, the therapy probe has a largest aperture dimension (e.g., FIG. 1A OD) that is 2 cm or greater. In other embodiments, the OD is greater than 5 cm. Accordingly, in one embodiment the OD is less than 10 cm. In yet another embodiment the OD is less than 7 cm.

In one embodiment, the therapy probe has a single ultrasonic therapy element, thereby providing a fixed focus to define the therapy region.

In one embodiment, the therapy probe is annular with a center cavity configured that is acoustically transparent in order to allow the imaging probe to image through the center cavity.

In one embodiment, the therapy probe and the imaging probe are configured to mate together coaxially. Coaxial probes are illustrated in FIG. 1A, disposed along axis A. As used herein, the term "mate" refers to an arrangement where the therapy probe and imaging probe are disposed within the same combined probe, as illustrated in FIGS. 1A and 1B. Similarly, FIGS. 3-6 illustrate a FIG. 1C illustrates non-coaxial probes, although in such a configuration the therapy probe 105 and imaging probe 110' are still synchronized to provide a therapy exposure and image the therapy region 115.

The imaging probe can be any imaging probe known to those of skill in the art that is sufficient to image the therapy region and synchronize with the therapy probe. Referring to FIGS. 1A and 1C, the imaging probe 110 or 110' has a height h and a width w. In one embodiment the height is from 1 cm to 2 cm. In one embodiment, the width is from 1 cm to 3 cm.

Imaging Synchronization

In one embodiment, the imaging probe and therapy probe are synchronized, such that imaging probe produces an imaging signal during an off period of the therapy exposure between pulses.

In one embodiment, the ultrasonic therapy system further comprises a switch configured to transition the ultrasonic therapy system from an imaging mode, wherein only the imaging probe is activated without the therapy probe, to a therapy mode, wherein the imaging probe and the therapy probe are both activated and synchronized to alternatingly produce an image of the therapy region and apply the therapy exposure to the therapy region.

In one embodiment, the ultrasonic therapy system is further configured to adjust a distance from the therapy probe to the start of the therapy region in response to changing a depth-of-focus of the imaging probe or vice versa.

Lenses

In one embodiment, the ultrasonic therapy system further includes a lens related to the therapy probe. A lens is essentially any material used to couple ultrasound to tissue. The lens is flat on the distal surface in one embodiment. In another embodiment the lens is convex on the distal surface. In another embodiment the lens is concave on the distal surface, thereby having a small cavity that can be filled with a gel or disposable pad.

In one embodiment, the lens is formed from a material selected from the group consisting of plastic, oil, ceramic, alcohol, water based fluid, gel, metal (e.g., aluminum), graphite, and combinations thereof. Representative plastics include siloxanes and urethanes. Particularly beneficial are polymers that can be polymerized at room temperature.

In one embodiment, the lens provides acoustic matching between the therapy probe and a therapy target.

Figure 12A:
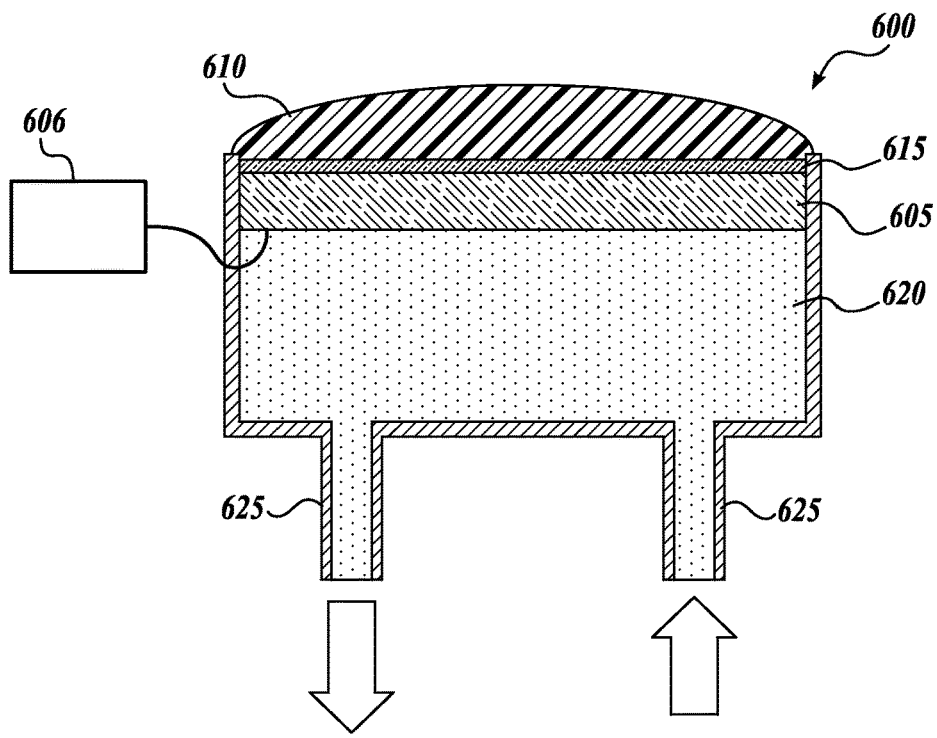
FIGS. 12A-12D schematically illustrate various embodiments of representative therapy probes having cooling systems incorporated therein in accordance with embodiments disclosed herein.

In another embodiment, a matching layer is included in between the transducer and the lens. See, for example, part 615 in FIG. 12A. The matching layer does not provide focusing but instead functions to transition impedance between the transducer and lens. Impedance mismatch will produce acoustic energy noise. Representative matching layer materials include composites, such as epoxies loaded with tungsten, aluminum or graphite.

Amplifier

In one embodiment, the ultrasonic therapy system further includes an amplifier configured to drive the therapy probe. The amplifier can be off-the-shelf or custom designed to produce the necessary power. An example of an amplifier incorporated into a representative system in FIG. 14. In one embodiment, the amplifier is configured to operate at a voltage (peak-to-peak) of 100 V to 3,000 V. In one embodiment, the amplifier is configured to operate at a (time average) power of 10 W to 1000 W. In one embodiment, the amplifier is configured to operate at a (time average) power of 20 W to 1000 W. In one embodiment, the amplifier is configured to operate at a (time average) power of 20 W to 500 W.

Cooling

In one embodiment, the ultrasonic therapy system further includes a cooling mechanism configured to remove heat from the therapy probe. FIGS. 12A-12D illustrate representative embodiments of probes 600 with incorporated cooling systems. Generally, the probe 600 includes a transducer 605, a lens 610, and a matching layer 615 between the transducer 605 and lens 610 to provide acoustic matching. An inlet and outlet 625 provides liquid or gas access to a cooling cavity 620.

An optional thermocouple 606 or other temperature measurement component is applied to the transducer 605 (FIG. 12A) or the lens 610 (FIG. 12B), or both (not pictured). The thermocouple 606 can be attached to a display in order to provide the operator with a visual indication of the temperature of the transducer 605, in case overheating is a danger, or the lens 610 if burning the patient's skin is a danger. The thermocouple can also be interfaced with a CPU or other system component in order to automate the indication of dangerous conditions or provide a feedback signal related to driving the transducer 605 (e.g., if the transducer 605 temperature rises dangerously the system will shut off the transducer 605, activate cooling, and/or warn the operator).

The cooling cavity 620 is filled with a gas (e.g., air) in one embodiment. In another embodiment, the cooling cavity is filled with a liquid (e.g., water). The gas or liquid can be circulated through the inlet and outlet 625 to provide improved cooling.

Figure 12B:
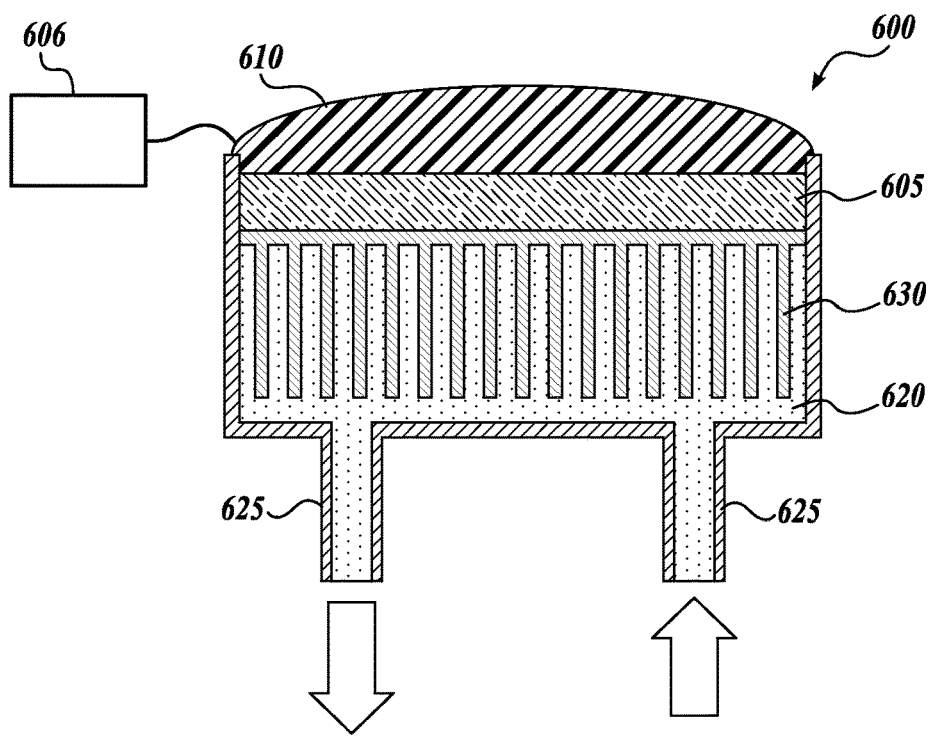

Referring to FIG. 12B, a heat sink 630 is interfaced with the transducer 605 to remove heat therefrom. A plurality of fins of the heat sink 630 extend into the cooling cavity 620 to dissipate heat further.

Figure 12C:
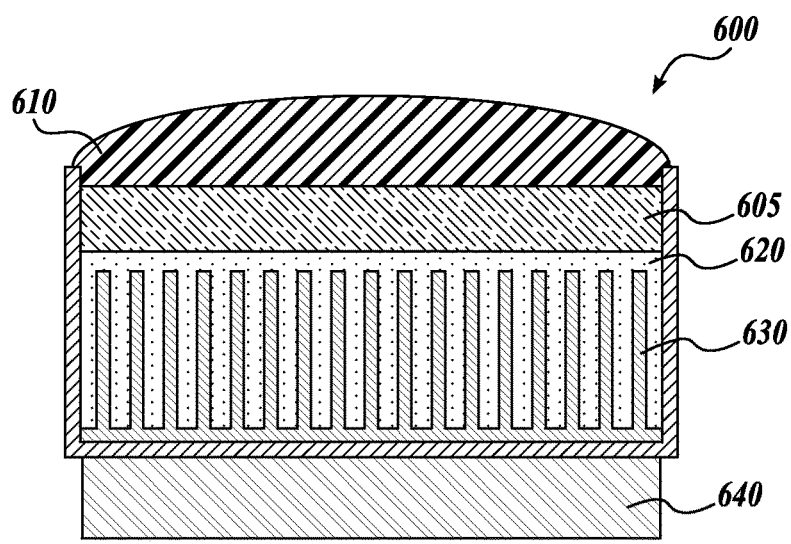

Referring to FIG. 12C the heat sink 630 is instead disposed on the opposite wall of the cooling cavity 620 from the transducer 605. A second heat sink 640 (or second portion of the first heat sink 630) is disposed on the outside of the cooling cavity 620 in order to dissipate heat transferred from the transducer 605, to the cooling cavity 620, through the first heat sink 630 and then second heat sink 640).

Figure 12D:
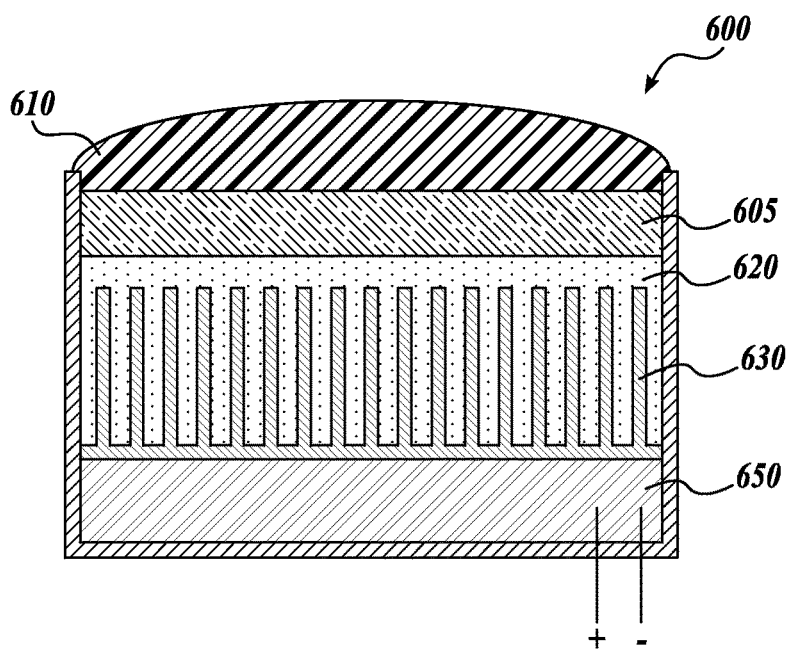

FIG. 12D is yet a further embodiment, which integrates a thermo-electric cooler 650 (TEC or Peltier element) to manage heat transferred from the transducer 605.

In one embodiment, the cooling mechanism is selected from the group consisting of air cooling, liquid cooling, a heat sink, a heat pipe, a thermo-electric cooler, and combinations thereof.

In one embodiment, the cooling mechanism is configured to remove heat from a portion of the therapy probe selected from the group consisting of a lens and an ultrasonic therapy element.

Central Processing Unit (CPU)

In one embodiment, the ultrasonic therapy system further includes a central processing unit (CPU) and a user interface, wherein the therapy probe, the imaging probe, and the user interface are each operatively connected through the CPU, and wherein the CPU is configured to control ultrasonic exposure from the therapy probe according to the user interface. The CPU can be any CPU known to those of skill in the art, such as a personal computer. The CPU may be used to coordinate the activities of the various system components (e.g., probes, amplifier, imaging), as described in more detail below with reference to FIG. 14.

In one embodiment, the imaging probe is configured to produce an ultrasound image of the therapy region on the user interface and wherein the imaging probe is synchronized with the therapy probe to obtain images of the therapy region in between pulses from the therapy probe.

In one embodiment, the CPU is configured to change the location or size of the therapy region via the therapy probe in response to input through the user interface.

Expanded System

Figure 14:
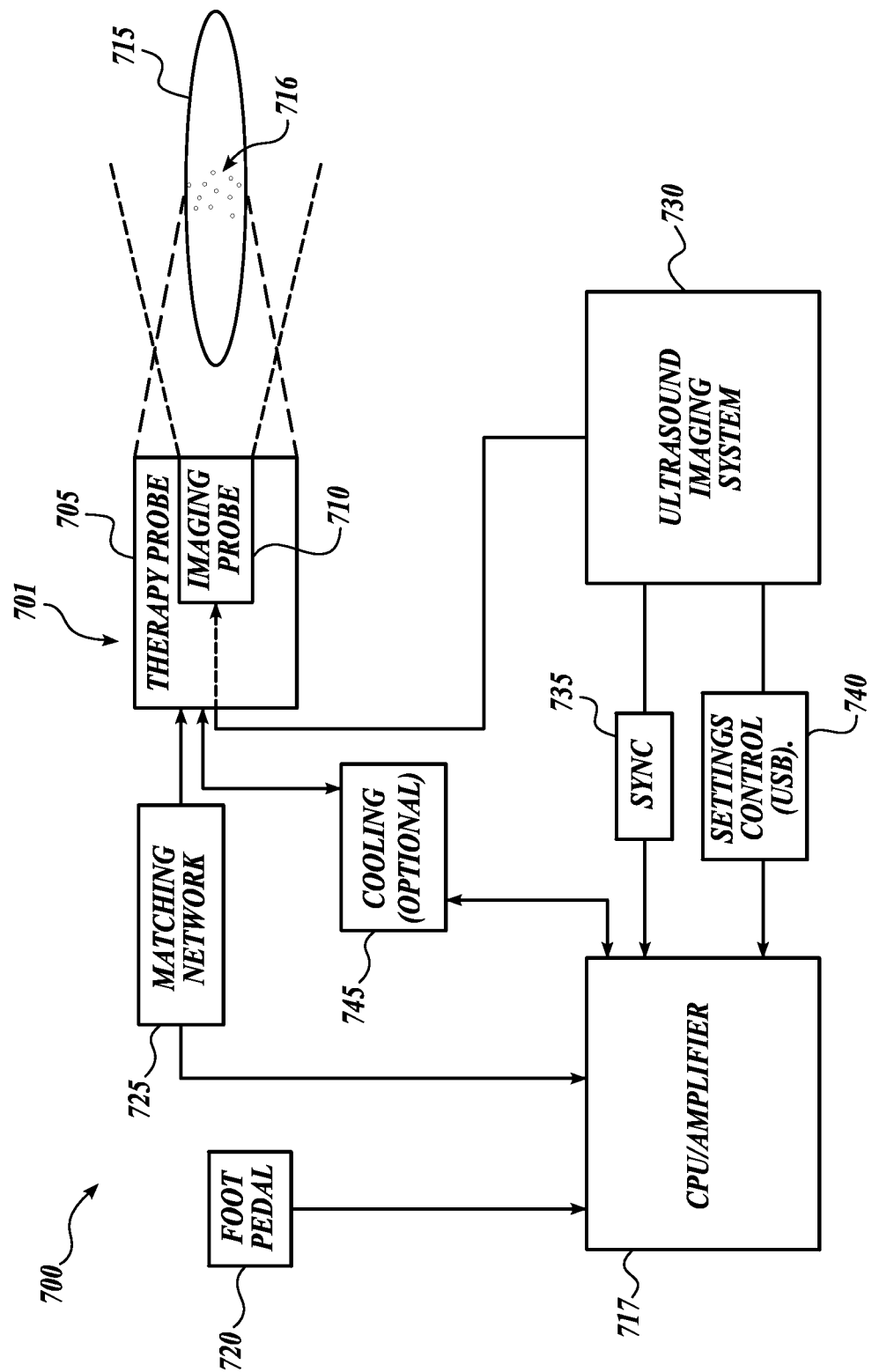
FIG. 14 is a block diagram depicting the components of a representative ultrasonic therapy system in accordance with embodiments disclosed herein.

FIG. 14 schematically illustrates an "expanded" system 700 that includes many of the components already disclosed. A combined probe 701 includes a therapy probe 705 and an imaging probe 710 imbedded therein. A therapy region 715 is illustrated as containing a plurality of targets (e.g., kidney stones). A CPU/amplifier 717 ultimately drives the therapy probe 705 and coordinates with the ultrasound imaging system 730 to coordinate the imaging probe 710 and therapy probe 705. The CPU and amplifier may be split into different components or may be combined in a single unit. The amplifier 717 can be activated by several mechanisms, with the mechanism in FIG. 14 being a foot pedal 720. During operation, a user presses a foot pedal 720 to activate the therapy exposure via the amplifier 717 and therapy probe 705. Use of the foot pedal 720 allows the user hands-free activation of the system 700. When the foot is removed from the pedal 720 the therapy exposure ceases. A number of pulses are emitted from the therapy probe 705 during the therapy exposure.

The amplifier 717 powers the therapy probe 705 via a matching network 725 that provides the appropriate power characteristics to the therapy probe 705 to generate the desired signal.

The imaging probe 710 provides imaging via an ultrasound imaging system 730 of the type known to those of skill in the art. Coordination with the amplifier 717 is made via a synchronization 735 bridge and setting and controls are coordinate 740 (e.g., by USB).

An optional cooling system 745 can be activated to cool the combined probe 701 and may receive input from a temperature sensor (e.g., a thermocouple). The cooling system 745 may interface with the CPU/amplifier 717 to shut off or reduce use of the therapy probe 705 if the temperature reaches a set limit. Or the sensor may be used to active the cooling system 745 to cool the therapy probe 705.

Probes

In another aspect, a combined probe is provided according to the embodiments shown and described. The probe includes a therapy probe and at least a cavity in which to coaxially dispose an imaging probe. In certain embodiments, the combined probe includes the imaging probe disposed within the cavity. The combined probe can be interfaced with an amplifier and imaging system as disclosed herein and can be used to perform the methods disclosed herein.

Methods

In another aspect, a method of moving one or more target objects using ultrasonic propulsion is provided. In one embodiment, the method includes applying a non-lithotriptic acoustic radiation force to a target object using an ultrasonic therapy system as shown and described herein. While the disclosed embodiments are primarily described in the context of moving kidney stones, it will be appreciated that the systems can be applied to move any small object within the appropriate range from the therapy probe. The target need not be in a living being.

In one embodiment, the target object is at least one in vivo kidney stone. The systems can be applied to patients in need in any manner useful to one of skill in the art. The systems are designed to ease the movement and eventual removal of kidney stones or fragments from the body. Therefore, the disclosed methods utilize the disclosed systems for moving one or more kidney stones.

In one embodiment, at least one the kidney stone is within a patient in an area selected from the group consisting of a kidney, a uretropelvic junction (UPJ), a bladder, a ureterovesicle junction (UVJ), and a ureter. These are the typical portions of a human in which one or more kidney stones may reside and whose removal the systems and methods can facilitate.

In one embodiment, the at least one kidney stone is moved a distance of at least 3 mm. This is a significant distance within a patient and indicates the broad moving effect of the systems and methods.

In yet a further embodiment, a plurality of kidney stones are simultaneously moved a distance of at least 3 mm. In this embodiment, the at least one kidney stone is a plurality of kidney stones and wherein the plurality of kidney stones are moved a distance of at least 3 mm during the therapy exposure time.

In another aspect, a method of moving one or more kidney stones in a therapy region using ultrasonic propulsion is provided. In one embodiment, the method includes using a broadly focused ultrasound therapy probe to apply a force on one or more kidney stones having a diameter of from 0.5 mm to 20 mm disposed within the therapy region, wherein the acoustic radiation force applied to each of the one or more kidney stones is from 50 µN to 0.5 N, and wherein the acoustic radiation force is not sufficient to fragment the kidney stones. This aspect is not necessarily tied to the exact devices disclosed herein, although such devices and systems are compatible with the present method. However, the present aspect at its most basic level is directed to use of broadly focused ultrasound to apply pressure to kidneys stones. In one embodiment, an imaging probe is synchronized with the therapy probe. This method is compatible with all of the systems, device, and methods disclosed elsewhere herein.

The following example is included for the purpose of illustrating, not limiting, the described embodiments.

EXAMPLES

Therapy Probe Design

In this Example we discuss single-element low-frequency design. Specifically, prior art lithotripsy and ultrasonic propulsion systems revealed the need and capability to expel clusters of stone fragments. These systems also failed to move large stones observably and did not detach stones. With the disclosed new single-element, broadly focused we can expel more fragments in a cluster more quickly. The change is an order of magnitude and enables 10× the number of pulses with each pulse 10× wider and spread across the entire stone cluster. The new design therefore also has more promise to detach and move large stones. These advances potentially cut treatment from hours to minutes and make ultrasonic propulsion clinically viable.

The shift from a prior art 128-element, 2-MHz imaging/pushing probe to a single element, low frequency (300 kHz) therapy probe enables displacing an entire cluster of stones. The imbedded imaging probe allows the user to observe fragment and cluster displacement while effectively sweeping a region stone free.

Advantages of lower frequency include:
Less focal heating=ability to send more pulses
Less attenuation through tissue or ribs
Higher intensities without nonlinear saturation
Broader beam=easier targeting and potential to move a pile of fragments
Potential to break stones off attachments as 300 kHz is used for comminution
The potential disadvantages are:
Cavitation is more likely at low frequency. Cavitation may injure tissue but also helps break stones. A cavitation monitor has been added.
Potentially less radiation force on <1 mm fragments at lower frequency but very little force is needed for such small stones.
Advantages of single-element, single focus include:
Minimize probe heating
Unique low cost therapy component
Standard unmodified ultrasound imaging hardware (don't have to "push" with the imaging probe)
Single user operation
The potential disadvantages are:
The user has to align the stone in the focus.
There are technical reasons most medical ultrasound is in the MHz range and comparatively little has been done at 300 kHz.

Several prototypes have been designed and built. All have a roughly annual therapy element at 330 kHz. In the hole in the middle is an imaging probe. This is a low frequency imaging probe for medical imaging and is not normally used for medical therapy. The thicker elements use more voltage. In addition, most applications of PZTs want one dimension much larger than the other 2 with the other two being about a wavelength. The thicker elements make it harder to do this and the risk is other modes taking energy and causing heating. One embodiment has a p7-4 imager, the other has a p4-2 imager, and the last has a linear 128 element imager centered at 4-5 MHz (p6-3 imager). These all tend to be higher frequency imagers than normally used for kidneys and they have a smaller field of view.

The overall footprint diameter is 5 cm or less. This size factor is important when considering the usability of the probe in a clinical context. First, the probe must be easily hand held and operable with one hand. Second the probe must be small enough to apply to a patient at several different points on the body, which requires a small probe that can mate with any skin surface.

We have a lens over the therapy probe that is selected for good energy transfer to the subject through proper matching of the acoustic properties and to reduce the modes. We built the lenses out of plastic, metal and graphite. The choice also affects the curvature of the face. We place the imaging probe at aperture of the curvature for best imaging (setting it back form the aperture reduces image quality but allows a smaller hole in the therapy probe). Then we use an acoustically transparent cover and either coupling gel or fluid in the space to make a flat face on the probe for coupling. This fluid might be used can optionally be used for cooling, too, and the cover can be disposable.

An exemplary combined probe is pictured in FIG. 1B, with this model referred having a convex hole and a relatively large (about 1×2 cm) imaging probe. The annular therapy probe is typically driven at 400 KHz. The annular, single element therapy transducer can be seen around the perimeter and the central feature is the imbedded imaging probe.

Another probe, the Propulse-2R is as follows: hand held, off the shelf P4-2 Philips phased array imaging probe that is removable from the central cavity of the probe; therapy probe is about 5 cm in diameter; imaging probe is coaxial; imbedded thermocouple on the therapy probe transducer; convex RTV (room temperature vulcanization) lens; and no cooling system.

Figure 1D:
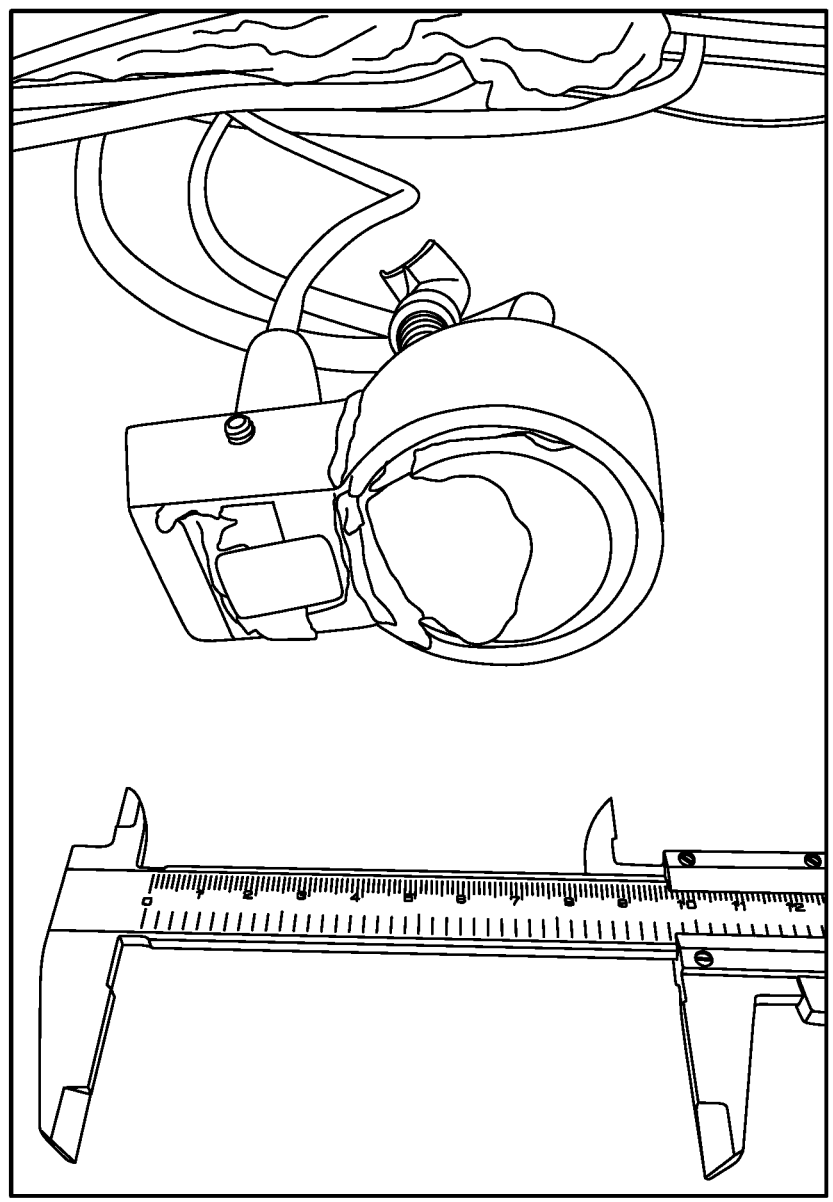
FIG. 1D is a photograph of a prototype combination of a non-axial therapy probe and imaging probe of the type illustrated in FIG. 1C.

Another exemplary combined probe includes a single element therapy transducer with an imaging probe on the side, as illustrated in FIG. 1C and pictured in FIG. 1D. The exemplary probe of FIG. 1D includes a concave aluminum lens, a 3D printed housing with a concave lens with water coupling, a second lens that is concave formed from RTV silicon.

Other variations utilized in experimental probes are as follows:

Cold-water cooling on the outside of the probe.

Backside cooling. Oil cooling on the back side of the therapy transducer. Forced air back cooling. Vortex back cooling A therapy-probe-only system was fabricated, with no imager.

Certain prototypes included a metal lens, cooling system, with and without latex, and a concave lens.

A system was fabricated wherein the imager and therapy probes were connected but not concentric.

Stacked transducers.

Porous ceramic and composite transducers.

1-16 element therapy elements on either side of an imaging probe

Redesigned imaging probes to make them flatter to have a farther focus, to lower the frequency, and to have better cooling.

Exemplary Test Results

Figure 8A:
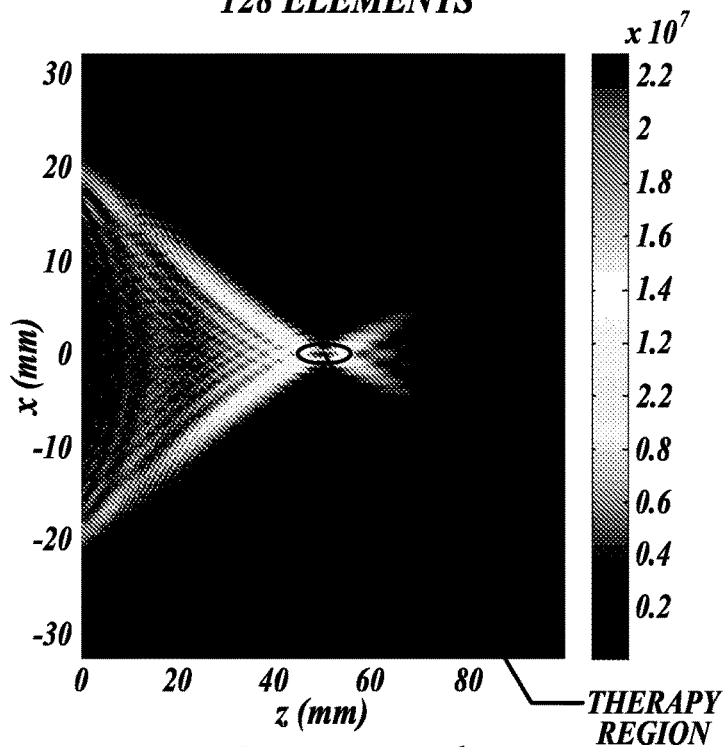
FIGS. 8A and 8B graphically illustrate simulated therapy region sizes generated by a 128 element prior art probe (FIG. 8A) and a single-element therapy probe in accordance with embodiments disclosed herein (FIG. 8B)
Figure 8B:
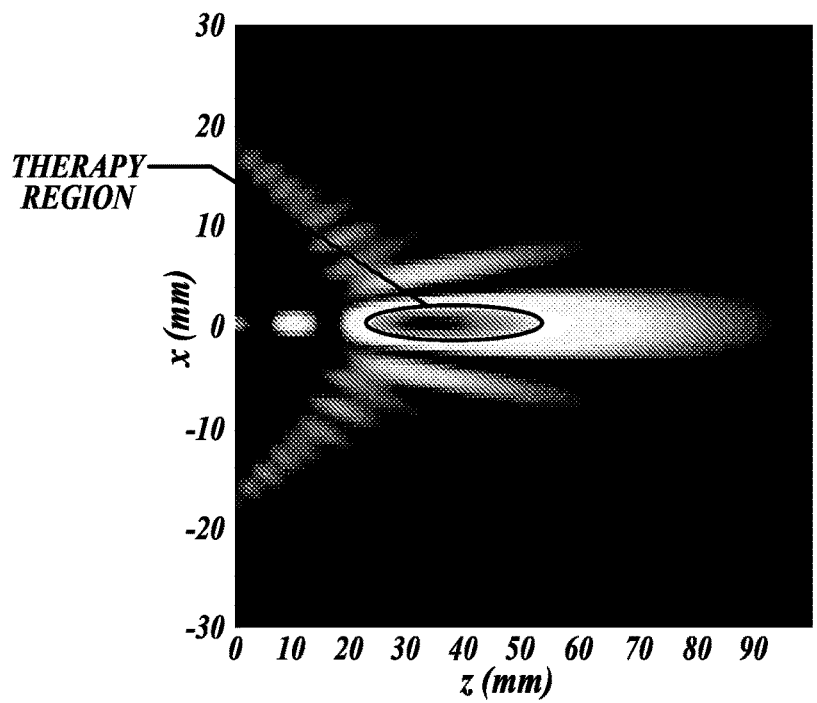

FIGS. 8A and 8B are graphical depictions of simulation data relating to a prior art therapy probe (FIG. 8A) and an exemplary probe (FIG. 8B). The simulation data were generated using the FOCUS ultrasound simulator from Michigan State University. Comparative FIG. 8A is a 128 element transducer operating at 2.4 MHz while exemplary FIG. 8B is a single transducer element operating at 400 kHz and dimensions of inner diameter 3 cm, outer diameter 5 cm, and geometric focus of 5 cm.

Because the figures are converted from color, the full data cannot be presented properly herein. However, a black line is drawn around the boundary in each figure showing the region of highest pressure, which defines the respective therapy regions.

Figure 9:
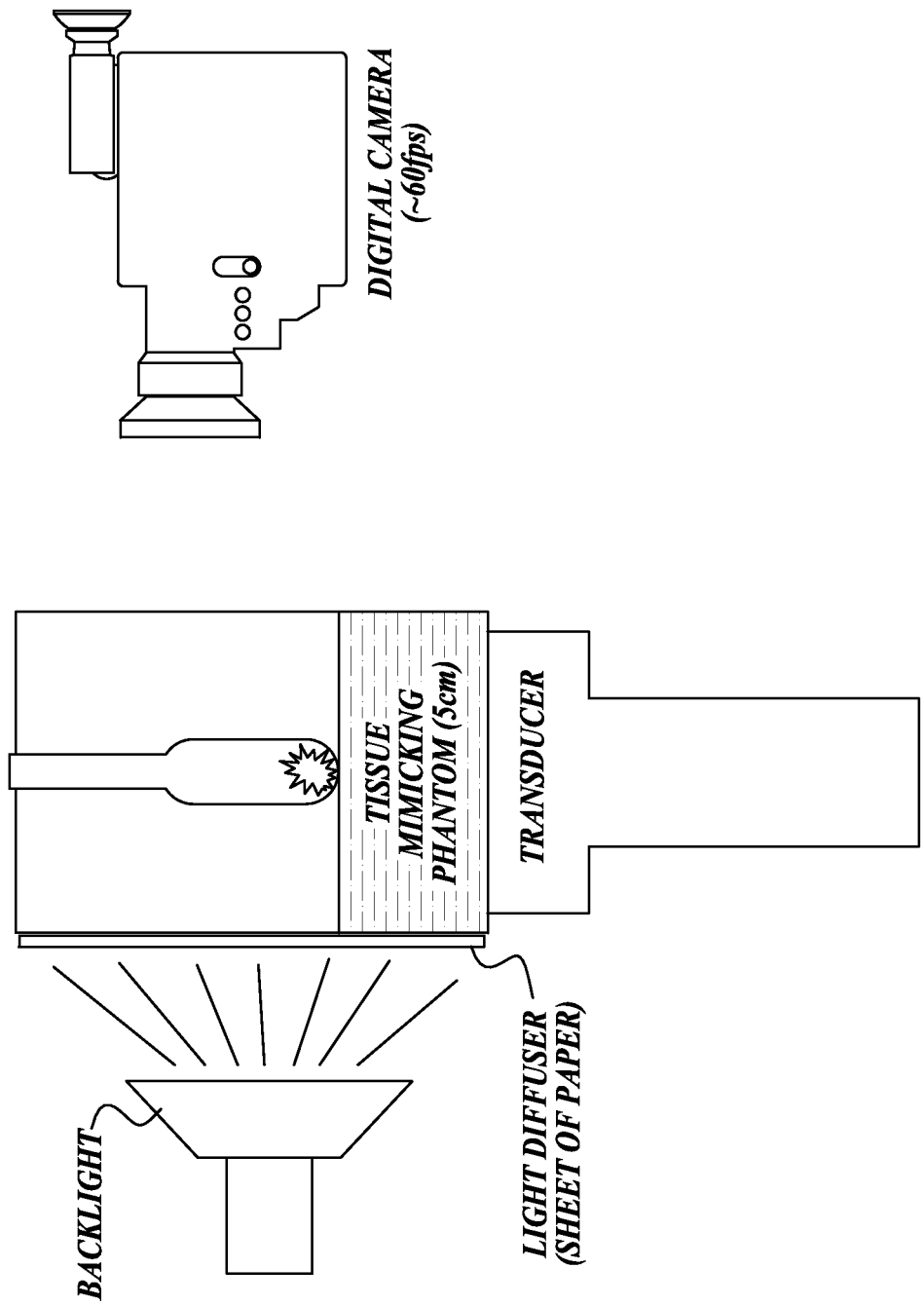
FIG. 9 schematically illustrates an experimental system for evaluating the efficacy of an ultrasonic probe in pushing one or more artificial kidney stones.
Figure 10:
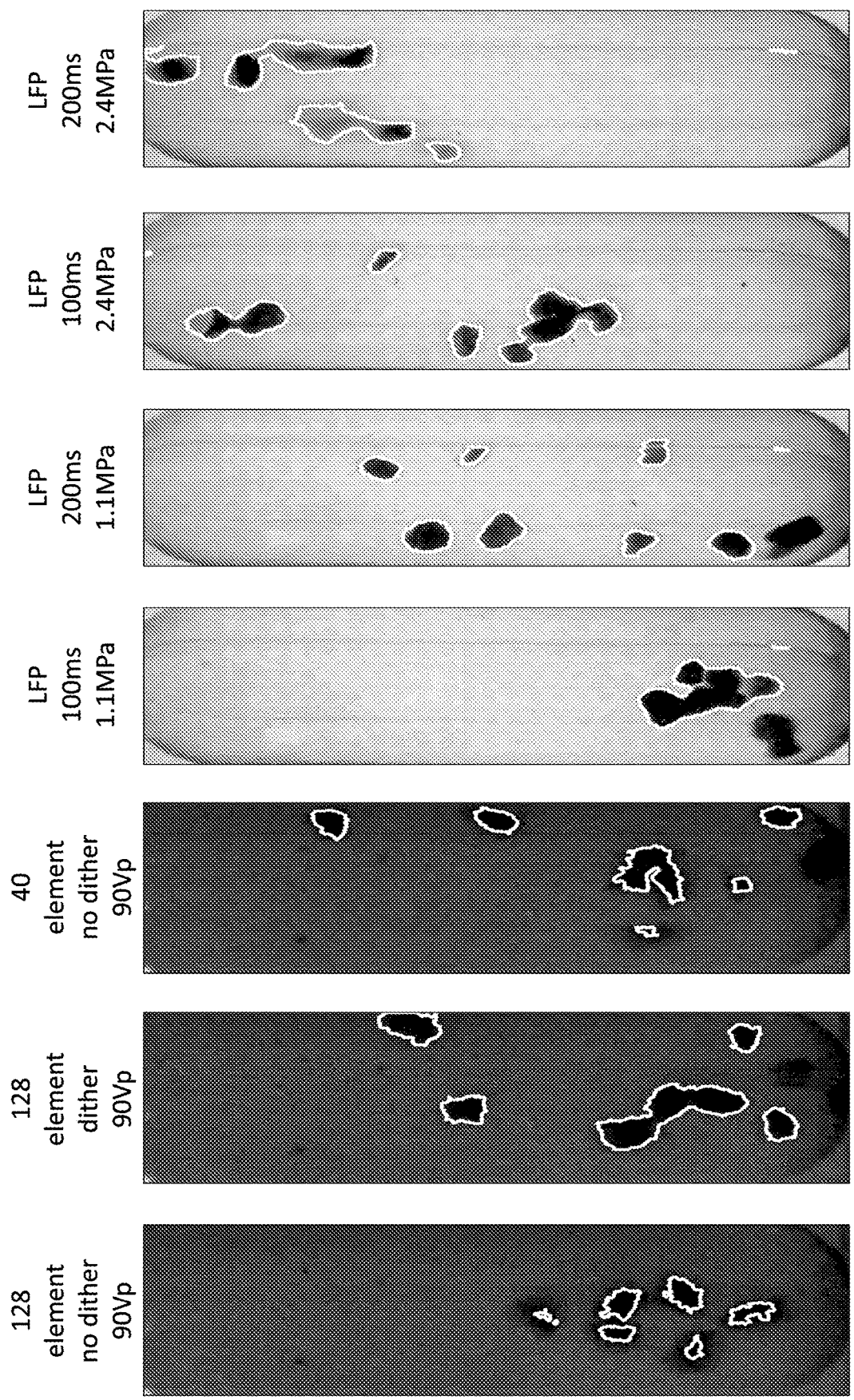
FIG. 10 is a series of photographs depicting experimental results comparing the ultrasonic pushing force of prior art and exemplary ultrasonic transducers.
Figure 11:
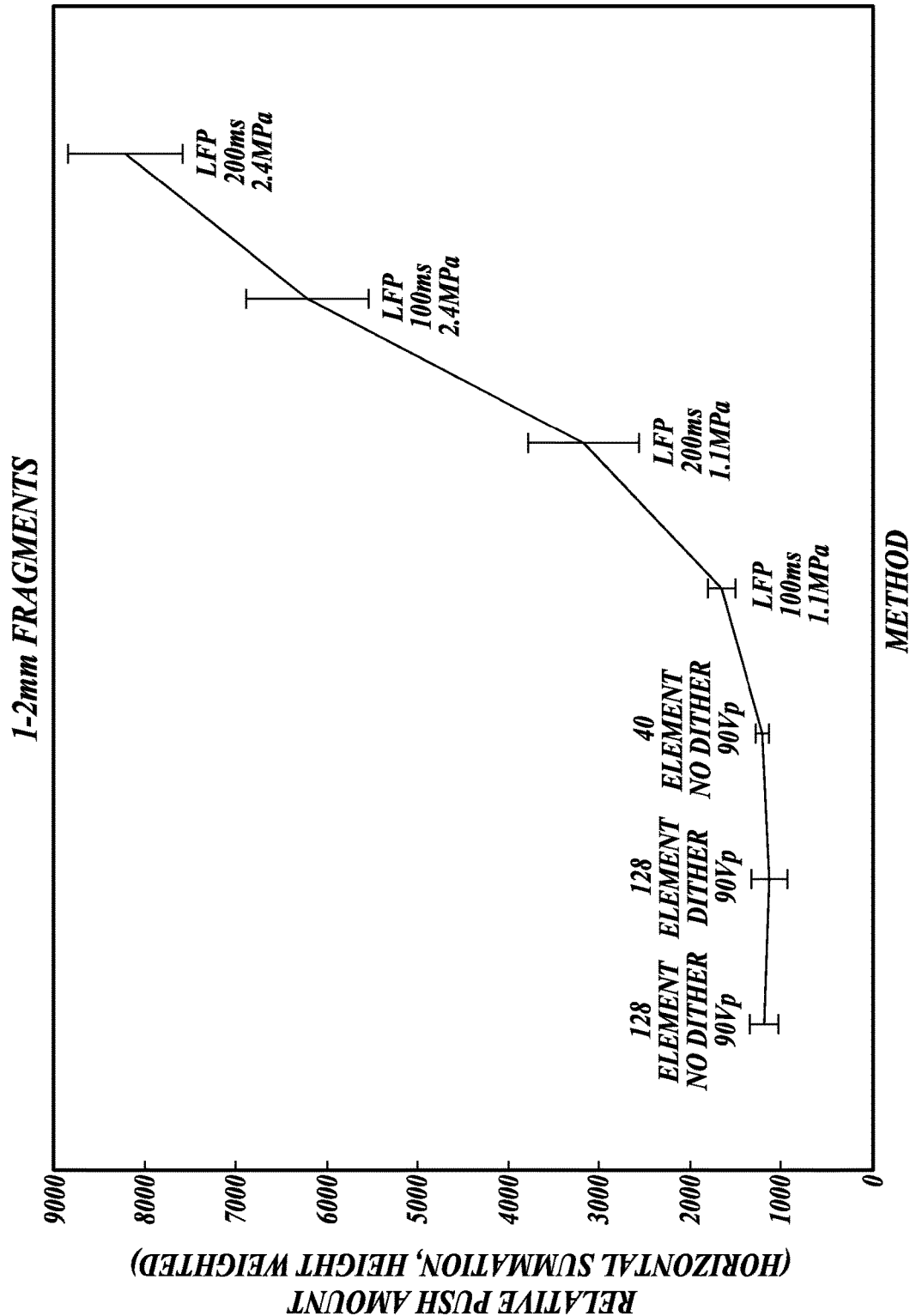
FIG. 11 graphically illustrates data collected from 10 iterations of the experiment illustrated in FIGS. 9 and 10 to determine the relative push strength of prior art and exemplary ultrasonic transducers.

FIGS. 9-11 relate to experimental testing to determine the "stone pushing" efficacy of the therapy probes (sometimes referred to herein as "LFP" or low-frequency pusher probes) according to the disclosed embodiments and compare them to prior art therapy probes. In order to accomplish this, an experimental design according to FIG. 9 was employed. Specifically, simulated kidney stones were pushed by a transducer while recording the "pushing" of the stones using a digital camera and subsequent image analysis.

In this example the stone fragments were created using BEGO simulated kidney stone material cement in 1 cm tall×6 mm diameter cylindrical molds. The hardened model stones were crushed into fragments and sieved into groups of 3-4 mm, 2-3 mm, 1-2 mm, and <1 mm, each having a sum mass of 80 mg. In addition there was a single model stone of 160 mg and a single model stone of 80 mg. Each group was placed into a pipette and filled with distilled and degased water.

Each pipette was placed vertical in a holder with a 5 cm phantom between the transducer and stones.

The phantom (IEC 60601-2-37) simulated human tissue with attenuation approximately 0.5 dB/cm/MHz and sound speed near 1540 cm/s.

A video camera was used to record the stone motion at approximately 60 fps.

Ten acquisitions were made for each system configuration and stone grouping. The exemplary LFP probe was operated at 350 kHz. Both the Propulse-I system (clinical system with the C5-2 diagnostic probe, 128 elements activated, dithered focal volume) and 40 element configuration (C5-2 diagnostic probe with 40 elements activated with no dithering) were operated at their maximum output power. The low frequency probe was tested at 1.1 MPa and 2.4 MPa and 100 ms and 200 ms. Each video frame was processed using two different methods. One method segmented all fragments separately, measured the height of the center of the fragments, and estimated the total volume of the fragment based upon the segmented cross-sectional area. The height was multiplied by the volume and summed for all segmented fragments in the field of view. This summed value is the metric for this method. This method does well for all methods where the fragments are >1 mm, but cannot segment the small pieces effectively. The second method simply thresholds the image appropriately, and takes a summation of all the resulting pixels scaled by their height.

FIG. 10 compiles still images at the endpoint (maximum pushed distance) of a test run for each of the transducers tested. The transducers were all tested using the same simulated kidney stones and related environment. The LFP transducers, particularly at higher pressures, were more effective at moving multiple stones longer distances. Relating these results back to the simulations of FIGS. 8A and 8B, the LFP transducers (FIG. 8B) produce a much larger therapy region, with higher pushing force on the stones, than traditional therapy probes (FIG. 8A). Until now, such a broad focus was not desirable.

FIG. 11 summarizes data for 10 sample runs of the type illustrated in FIG. 10, in order to numerically characterize the efficacy of the transducers. The Y-axis relates to Relative Push Amount, which is calculated by averaging 10 push runs. It is the sum of the heights of the dark pixels (pixels related to stone) and standard deviation error bars. As was seen in FIG. 10, the LFP transducers according to the disclosed embodiments provided significantly superior pushing force on the stones. The unusual and unexpected efficacy of the inventive transducers compared to the prior art is apparent when viewing FIG. 11

While illustrative embodiments have been illustrated and described, it will be appreciated that various changes can be made therein without departing from the spirit and scope of the invention.

The invention claimed is:

1. A method for moving a kidney stone by an ultrasonic therapy, the method comprising:
   moving the kidney stone by applying a non-lithotriptic acoustic radiation, wherein applying the non-lithotriptic acoustic radiation comprises the steps of:
   (1) producing, by a therapy probe, a therapy exposure comprising one or more therapy pulses at:
      (i) a frequency of 200 kHz to 500 kHz;
      (ii) therapy exposure time of at least 10 ms; and
      (iii) a peak negative pressure in the therapy region of 1 MPa to 4 MPa;
   (2) applying therapy pulses within a therapy exposure time of the therapy pulses;
   (3) subjecting a therapy region to the therapy pulses, wherein the therapy region of one pulse defines a volume subjected to a full-width half-maximum pressure or greater, and wherein the therapy region has a length of 2 cm or greater in an axial direction and 2 mm or more in width;
   (4) applying an acoustic radiation force from 50 μN to 0.5 N by the therapy pulses on the kidney stone;
   (5) using the acoustic radiation force, actively moving the kidney stone over the therapy region;
   (6) ultrasonically imaging the therapy region by an imaging probe, wherein the imaging probe and the therapy probe are synchronized to alternatingly image and treat the therapy region; and
   (7) based on ultrasonically imaging of the therapy region, adjusting a location or size of the therapy region prior to additional applying of the non-lithotriptic acoustic radiation by the therapy probe;
   wherein the therapy probe comprises a therapy transducer;
   wherein a lens is disposed over the therapy transducer;
   wherein a matching layer is in direct contact with the therapy transducer and the lens;
   wherein the matching layer is configured to provide an acoustic matching between the therapy transducer and the lens;
   wherein a housing is configured to encompass and carry the therapy probe and the imaging probe; and
   wherein the therapy probe and the imaging probe are adjacent to each other.

2. The method of claim 1, further comprising producing an average power of 10 W to 200 W for 1 second to 10 min.

3. The method of claim 1, wherein the therapy exposure is a single continuous pulse.

4. The method of claim 1, wherein the therapy exposure comprises a therapy burst that comprises a plurality of pulses separated by off periods.

5. The method of claim 1, wherein the therapy probe has a largest aperture dimension that is 5 cm or less.

6. The method of claim 1, wherein the therapy probe has a single ultrasonic therapy element, thereby providing a fixed focus to define the therapy region.

7. The method of claim 1, wherein the therapy probe is annular with a center cavity configured that is acoustically transparent in order to allow the imaging probe to image through the center cavity.

8. The method of claim 1, wherein the therapy probe and the imaging probe are configured to mate together coaxially.

9. The method of claim 1, further comprising synchronizing the imaging probe and the therapy probe such that imaging probe produces an imaging signal during an off period of the therapy exposure between pulses.

10. The method of claim 9, further comprising transitioning the ultrasonic therapy system from an imaging mode to a therapy mode by a switch, wherein, in the imaging mode, only the imaging probe is activated without the therapy probe, and wherein, in the therapy mode, the imaging probe and the therapy probe are both activated and synchronized to alternatingly produce an image of the therapy region and apply the therapy exposure to the therapy region.

11. The method of claim 9, further comprising adjusting a distance from the therapy probe to the start of the therapy region in response to changing a depth-of-focus of the imaging probe or vice versa.

12. The method of claim 1, wherein the lens provides acoustic matching between the therapy probe and a therapy target.

13. The method of claim 1, further comprising driving the therapy probe by an amplifier.

14. The method of claim 1, further comprising removing heat from the therapy probe by a cooling mechanism.

15. The method of claim 14, wherein removing heat from the therapy probe comprises removing heat from a lens or an ultrasonic therapy element.

16. The method of claim 1, wherein the therapy probe, the imaging probe, and a user interface are each operatively connected through a CPU, and wherein the method further comprising controlling ultrasonic exposure from the therapy probe by the CPU according to the user interface.

17. The method of claim 16, further comprising producing, by the imaging probe, an ultrasound image of the therapy region on the user interface, wherein the imaging probe is synchronized with the therapy probe to obtain images of the therapy region in between pulses from the therapy probe.

18. The method of claim 16, further comprising changing the location or size of the therapy region via the therapy probe in response to input through the user interface.

19. The method of claim 1, wherein the therapy probe peripherally surrounds the imaging probe.

20. The method of claim 1, wherein the imaging probe fits through an aperture in the therapy probe.

* * * * *